(12) United States Patent
Kost et al.

(10) Patent No.: US 12,403,334 B2
(45) Date of Patent: Sep. 2, 2025

(54) LOW INTENSITY ULTRASOUND THERAPY

(71) Applicant: B.G. NEGEV TECHNOLOGIES AND APPLICATIONS LTD., AT BEN-GURION UNIVERSITY, Beer Sheva (IL)

(72) Inventors: Joseph Kost, Omer (IL); Aharon (Roni) Azagury, Kiryat Gat (IL); Yana Yudilevich, Beer Sheva (IL); Eden Bergman, Machane Adi (IL); Tamar Traitel, Beer Sheva (IL); Rivka Goldbart, Lehavim (IL); Itay Rousso, Even Yehuda (IL); Moshe Elkabets, Kibbutz Beit Kama (IL)

(73) Assignee: B G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 822 days.

(21) Appl. No.: 17/249,638

(22) Filed: Mar. 8, 2021

(65) Prior Publication Data

US 2021/0213307 A1     Jul. 15, 2021

Related U.S. Application Data

(63) Continuation-in-part of application No. 14/198,701, filed on Mar. 6, 2014, now Pat. No. 10,960,233.

(60) Provisional application No. 61/773,169, filed on Mar. 6, 2013.

(51) Int. Cl.
    *A61N 7/02*          (2006.01)
    *A61N 7/00*          (2006.01)

(52) U.S. Cl.
    CPC ...... *A61N 7/022* (2013.01); *A61N 2007/0004* (2013.01); *A61N 2007/0073* (2013.01)

(58) Field of Classification Search
    CPC ............ A61N 7/022; A61N 2007/0004; A61N 2007/0073; A61N 7/00; A61N 2007/0034
    See application file for complete search history.

(56) References Cited

U.S. PATENT DOCUMENTS

| | | |
|---|---|---|
| 6,589,173 B1 | 7/2003 | Mitragotri |
| 7,481,781 B2 | 1/2009 | Craig et al. |
| 2002/0004052 A1 | 1/2002 | Berd et al. |

(Continued)

FOREIGN PATENT DOCUMENTS

WO    WO2006/051542      5/2006

OTHER PUBLICATIONS http://physicaltherapyweb.com/therapeutic-ultrasound, retrieved Nov. 7, 2016.

(Continued)

*Primary Examiner* — Hien N Nguyen
(74) *Attorney, Agent, or Firm* — Nixon & Vanderhye PC

(57) ABSTRACT

Provided herein methods for treating a subject suffering from a disease or a disorder associated with hyperproliferating cells, by irradiating the cells with low-frequency ultrasound at an intensity that is either below the cavitational threshold intensity for the ultrasound frequency, or is characterized by a low-frequency mechanical index below 2.5. The methods may further comprise determining an elasticity value of the cells, and adjusting the ultrasound intensity accordingly.

7 Claims, 23 Drawing Sheets

(56) References Cited

U.S. PATENT DOCUMENTS

| | | | |
|---|---|---|---|
| 2002/0192221 A1* | 12/2002 | Roach | C07K 16/18 |
| | | | 604/20 |
| 2004/0187876 A1* | 9/2004 | Myhr | A61N 7/022 |
| | | | 128/898 |
| 2005/0054958 A1 | 3/2005 | Hoffmann | |
| 2007/0088345 A1 | 4/2007 | Larson et al. | |
| 2008/0056937 A1 | 3/2008 | Cordemans de Meulenaer et al. | |
| 2008/0071312 A1 | 3/2008 | Ridgway | |
| 2010/0092424 A1 | 4/2010 | Sanghvi et al. | |
| 2011/0178441 A1 | 7/2011 | Tyler | |
| 2013/0129799 A1* | 5/2013 | Shibaguchi | A61K 41/0033 |
| | | | 514/185 |
| 2013/0131432 A1 | 5/2013 | Kline | |
| 2015/0306429 A1* | 10/2015 | Towe | A61N 7/00 |
| | | | 601/2 |

OTHER PUBLICATIONS

Healing sound: the use of ultrasound in drug delivery and other therapeutic applications, by Sarnir Mitragotri, published in Nature Reviews—Drug Discovery, vol. 4, Mar. 2005, pp. 255-260.
Kennedy, "High-intensity focused ultrasound in the treatment of solid tumors," Nature Reviews: Cancer, vol. 5, Mar. 18, 2005, pp. 321-327.
Sponer, "Dependence of the Cavitation Threshold on the Ultrasonic Frequency," Czech J. Phys., vol. 40: 1123-1132 (1990).
Kenneth S. Suslick: Ultrasonic-Its Chemical, Physical and Biological Effects, NY VCH publications, pp. 20 and 311, 1988.
Ahmadi et al., Progress in Biophysics and Molecular Biology 108 (2012), "Bio-effects and safety of low-intensity, low-frequency ultrasonic exposure," pp. 119-138, journal homepage: www.elsevier.com/locate/pbiomolbio.
Hedrick et al., "An Overview of Thermal and Mechanical Acoustic Output Indices," JDMS 9; pp. 228-235; Sep./Oct. 1993.

* cited by examiner

LOW INTENSITY ULTRASOUND THERAPY

This application is a continuation-in-part (CIP) of U.S. application Ser. No. 14/198,701 filed Mar. 6, 2014, which claims priority to U.S. Provisional Application No. 61/773,169 filed Mar. 6, 2013, the entire contents of each of which are hereby incorporated by reference.

FIELD OF THE INVENTION

The present disclosure relates generally to the field of treatment of hyperproliferative diseases and disorders. More specifically, methods of treating a subject afflicted with cancer, neoplasms or metastatic cancer using ultrasound are disclosed.

BACKGROUND OF THE INVENTION

Ultrasound has been used for several decades in the medical field, mostly as a diagnostic tool, and to a lesser extent as a therapeutic device.

In most therapeutic methods ultrasound has been applied topically, either externally (on the skin surface) or internally (tympanal, buccal, vaginal or nasal applications). The common feature in this type of application is that the therapeutic effect results from increasing the penetration of the membrane, thereby enabling the delivery of medicines and/or other therapeutic agents. Another application of ultrasound which relies on enhancing the skin permeability is to increase the delivery out of the skin (namely for sensing purposes), thereby enhancing the sensitivity of measurement techniques (for example, measuring glucose levels on the skin). All of these methods require low intensity ultrasound, so that to avoid damaging the skin more than needed to increase its permeability, and have a short range of impact.

In some cases, ultrasonic therapy uses focused, localized heating to selectively destroy tissue anomalies. Heating a tissue beyond a critical temperature for a period of time causes necrosis, the destruction of tissue. Therefore, another type of therapeutic application of ultrasound is by using High Intensity Focused Ultrasound (HIFU), which is used to affect inner organs, mostly by ablation, without affecting the skin or intermediate membranes and/or tissues. Clinical HIFU procedures are typically performed in conjunction with an imaging procedure to enable treatment planning and targeting before applying a therapeutic or ablative levels of ultrasound energy. When Magnetic resonance imaging (MRI) is used for guidance, the technique is sometimes called Magnetic Resonance-guided Focused Ultrasound, often shortened to MRgFUS or MRgHIFU.

During the last decade many studies have concentrated on cancer treatment. Some of these studies focused on non-invasive, targeted treatment of cancerous cells by utilizing different triggers and drug carriers. Moreover, some applications, like ultrasound, have been tested for their ability to enhance drug release and carriers penetration into tumors. Other studies focused on identifying the effect of ultrasound on cancerous cells, albeit without comparing its effect on normal cells.

Specifically, ultrasound was used for cancer treatment in a number of methods which include: tumor exposure to ultrasound directly and indirectly (using HIFU) in order to increase drug or carrier/drug penetration into tumors, drug carriers exposure to ultrasound as a trigger for drug release and even tumor ablation by HIFU. For example, HIFU in the treatment of solid tumors is described by James E. Kennedy in Nature Reviews Cancer, published online 18 Mar. 2005, pages 321-327.

At high enough acoustic intensities, both cavitation (abrupt microbubble formation as a result of liquid medium exposure to ultrasound) and temperature elevation can occur, which in turn, cause various kinds of tissue damage. Because the onset of cavitation and the resulting tissue damage can be unpredictable, it has generally been avoided in clinical applications. Furthermore, a disadvantage of methods relying on ablation and/or thermal elevation is that the tissue damage is not limited to the cancerous tissue, but unselectively affects all the neighboring healthy tissue within the treated area.

Several methods have been suggested to address this non-selectivity of ablation:

U.S. Pat. No. 7,481,781 disclosed the combined use of an electric field and ultrasound to ablate a cell or tissue.

PCT Publication No. WO 2006/051542 disclosed exposing nanoparticles to electromagnetic radiation under conditions wherein the nanoparticles generate microbubbles which emit heat when exposed to ultrasonic radiation.

US Patent Application No. 2013/0131432 disclosed a method to use Tuned resonant frequency ultrasound ("TRFU") at intensities as high as $10^7$ W/cm$^2$, for the treatment of cancer that selectively destroys neoplastic cells while leaving surrounding healthy tissue minimally affected. TRFU is based on the calculation of a resonant frequency according to the size of the cellular structure targeted for disruption. Namely, for certain types of cancerous cells, a resonance frequency is calculated, and the intensity is fitted accordingly, thereby reducing or eliminating the neoplastic cells. However, this method is "blind" to cancerous cells having the same size of normal cells, and furthermore the frequencies taught in this application are unconventionally high for therapeutic uses, and reach 16 MHz and higher.

However, none of the studies conducted so far have been able to provide a therapeutically non-invasive selective treatment method of cancer and/or other proliferative diseases, which will avoid causing damage to a healthy tissue, cells or organs, while being solely based on ultrasound at low intensities, as opposed to HIFU, which is also non-invasive, but uses high intensities of ultrasound, and avoided damage to tissues only by its focusing mechanism.

There is therefore a continuing need to find alternative therapeutically selective non-invasive treatment method of cancer and/or other proliferative diseases, which relies solely on ultrasound at low intensities.

Figure 4:
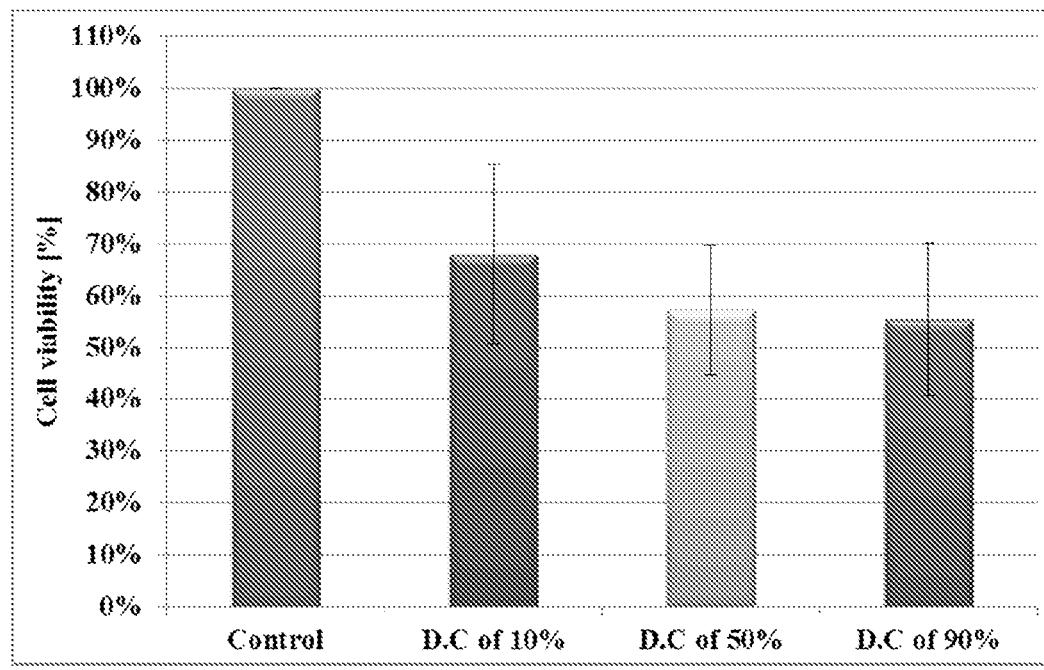
Figure 5:
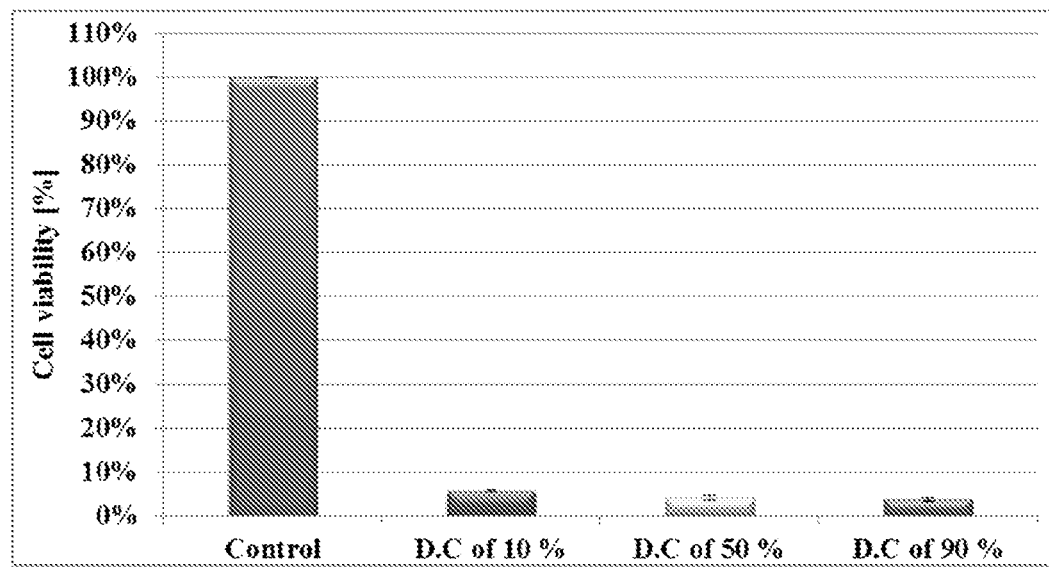
Figure 6:
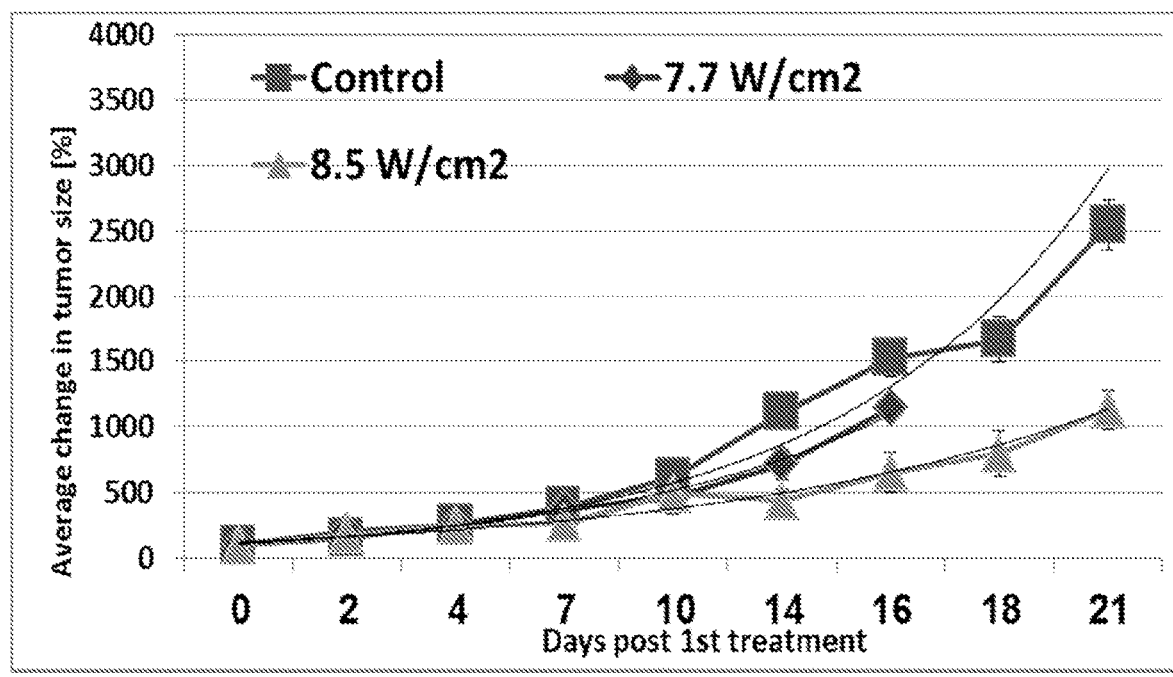

W/cm², 4.38 W/cm² and 5.09 W/cm², respectively) and durations. P value<0.1 compared to control experiment;

FIG. 4 shows MCF10A cell type average viability after 5 minutes exposure to ultrasound (20 kHz) at 5% amplitude (5.09 W/cm²) for different US duty cycles (10%, 50% and 90%). P value<0.1 compared to control experiment;

FIG. 5 shows NAR cell type average viability after 5 minutes exposure to ultrasound (20 kHz) at 5% amplitude (5.09 W/cm²) for different US duty cycles (10%, 50% and 90%). P value<0.1 compared to control experiment; and FIG. 6 shows the percentage of change in KHJJ tumor size in vivo (compared to tumor size pre first insonation) post US exposure (20 kHz and 50% DC) at two US intensities (7.7 and 8.5 W/cm²) and in a control group.

Figure 7A:
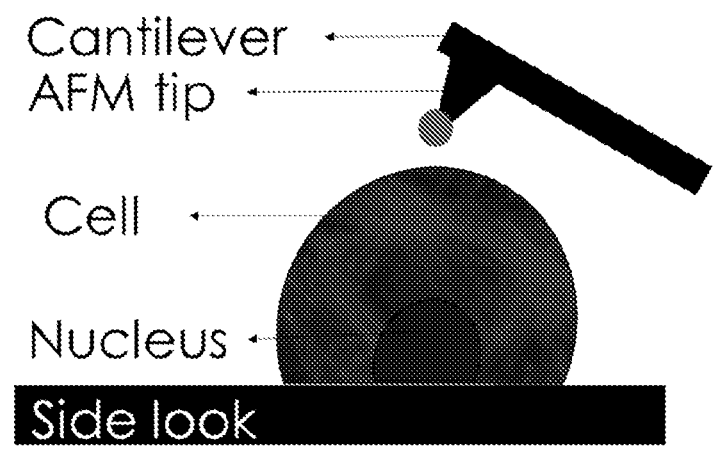
Figure 7B:
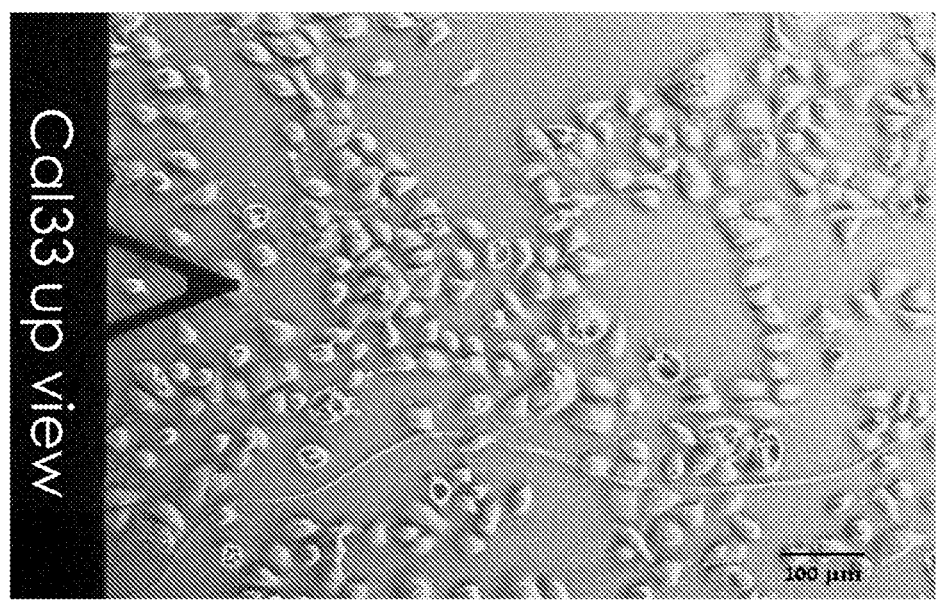
Figure 7C:
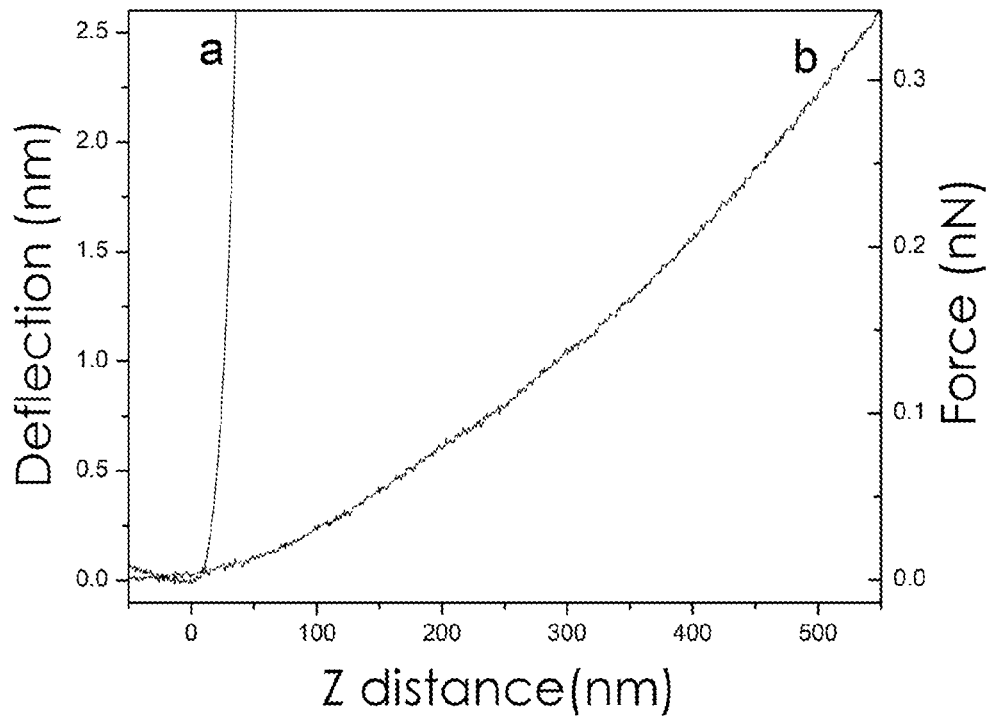
Figure 7D:
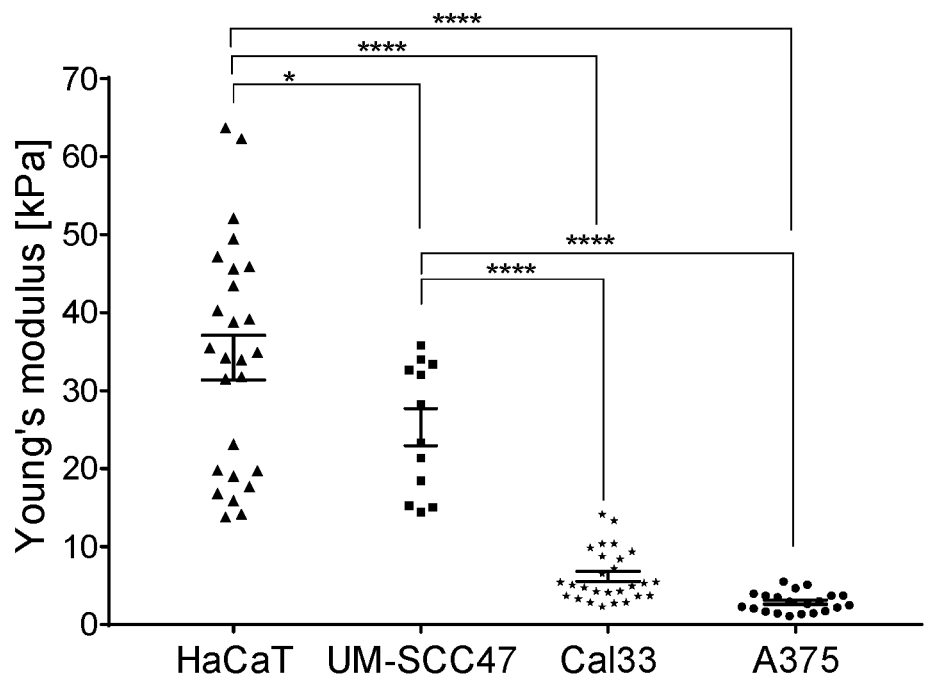
Figure 7E:
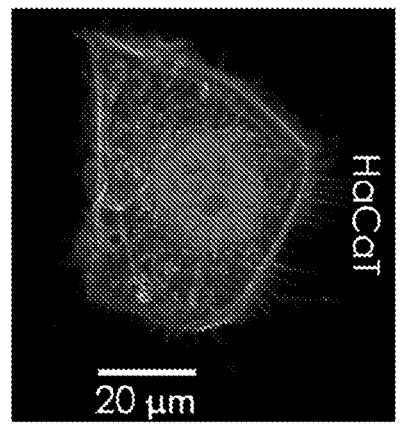

FIG. 7A-FIG. 7G: FIG. 7A is a schematic illustration of an AFM deflection measurement setting; FIG. 7B is a representative micrograph of Cal33 cell line during AFM measurement (optical microscope, brightfield mode, ocular magnification was 10× and the objective magnification was 10×, in total the magnification was 100×). FIG. 7C is a representative example of deflection-distance plot obtained by AFM analysis for HaCaT cell, using Matlab analysis based on Hertz model as elaborated, e.g. in Lekka M., BioNanoSci. (2016) 6:65-80, doi 10.1007/s12668-016-0191-3: plot (a) was obtained for hard, non-deformable surface (glass) and plot (b) obtained for HaCaT cell. FIG. 7D is a graph showing the calculated Young's modulus of different types of cancerous (Cal33 and A375) and non-cancerous (HaCaT) superficial cells at 37° C. Error bars indicate SEM. Each dot is an average of three measurements at different areas on the same cell (60 force-distance curves total). Statistical significance was calculated using one-way ANOVA test, *p<0.05, ****p<0.0001. Confocal images of different types of superficial cancerous and non-cancerous cells with labeled F-actin as shown in FIG. 7E (HaCaT (keratinocytes)); in FIG. 7F (Cal33 (HNSCC)); and in FIG. 7G (A375 (melanoma)). The F-actin was labeled in red and the nucleus was labeled in blue.

Figure 8A:
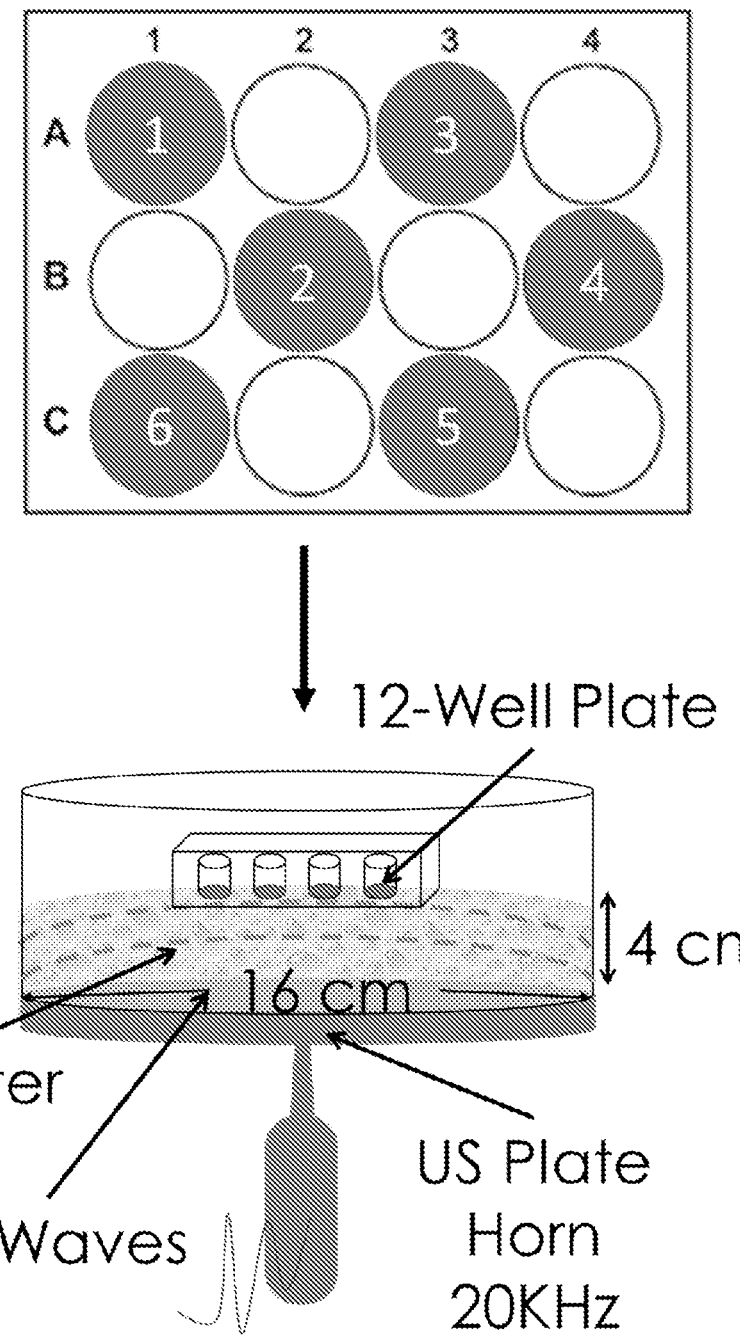
Figure 8B:
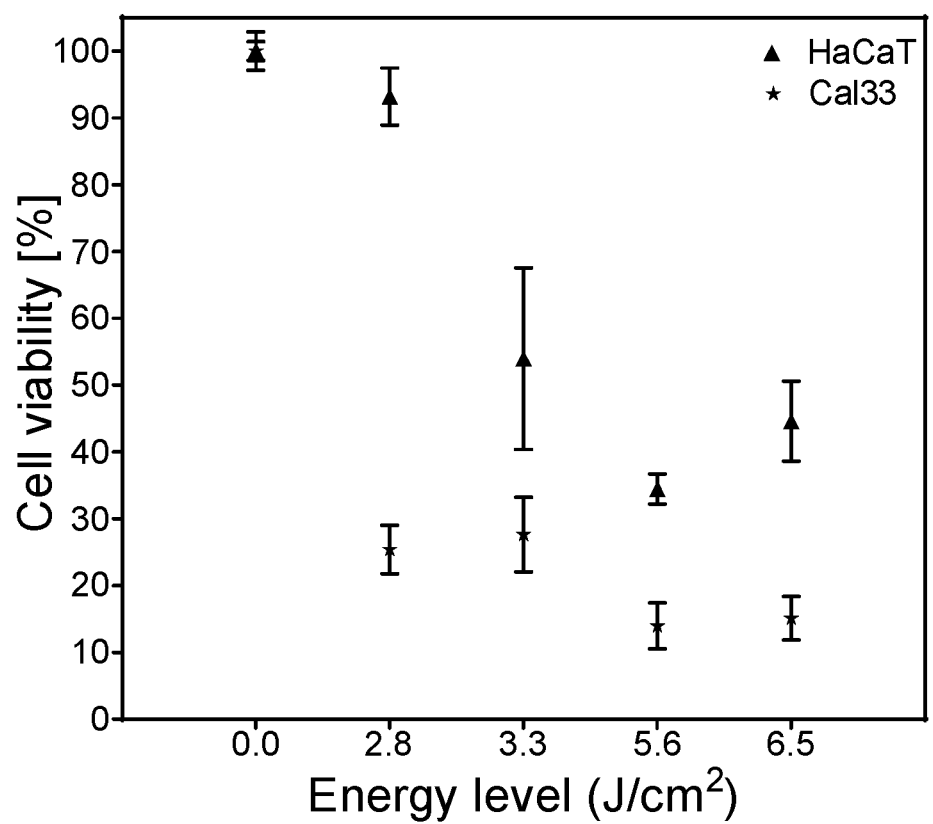
Figure 8C:
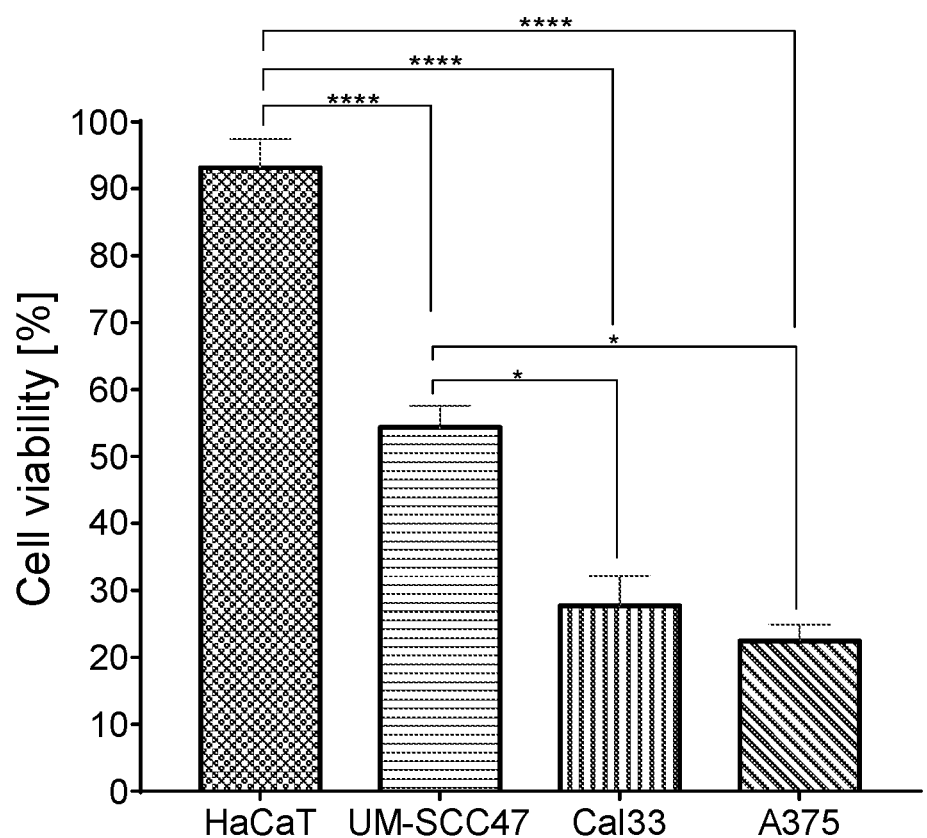
Figure 8D:
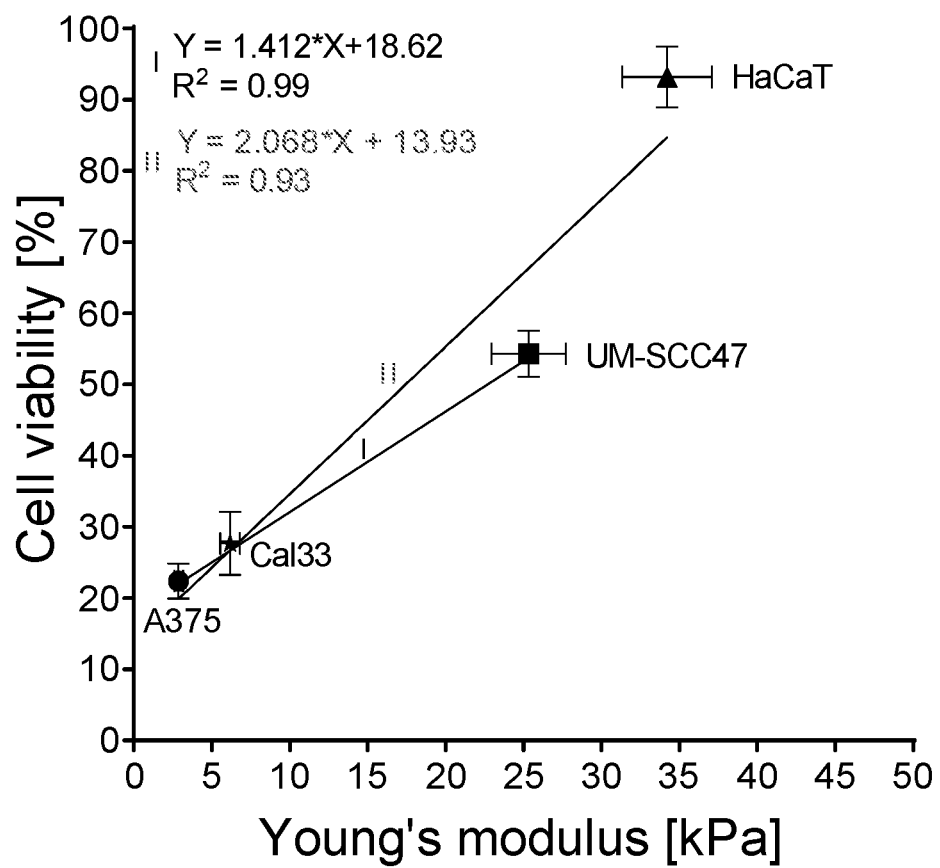

FIG. 8A-FIG. 8D: FIG. 8A is a schematic representation of an experimental setup, in which the upper part illustrates cell seeding in a 12 well tissue culture plate at specific wells and respective seeding order, and the lower part illustrates an ultrasound (US) plate horn set-up (20 KHz). FIG. 8B is a graph showing cell viability percentage of non-cancerous keratinocytes cells (HaCaT) compared to superficial HNSCC cells (Cal33) for US conditions: intensity of 0.139-0.164 W/cm², 20 and 40 sec application time, and 50% duty cycle. Statistical significance was calculated using Two-way ANOVA test, where *p<0.05, p<0.01, *p<0.001, and ****p<0.0001. FIG. 8C is a bar graph showing cell viability percentage of different superficial cancer cell lines in vitro, at constant intensity of 0.139 W/cm² during 20 sec application time and 50% duty cycle. Statistical significance was calculated using one-way ANOVA test, with post-hoc Sidak's multiple comparisons test where *p<0.05, p<0.01, *p<0.001, and ****p<0.0001; FIG. 8D is a graph showing a correlation between viability percentage of different cell lines (non-cancerous and cancerous cells) after exposure to US in a fixed operation conditions (20 sec, 50% duty cycle and 0.139 W/cm²) and the average value of calculated Young's modulus.

Figure 9A:
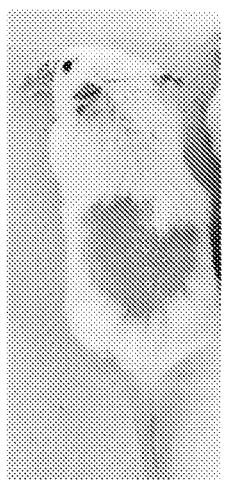
Figure 9B:
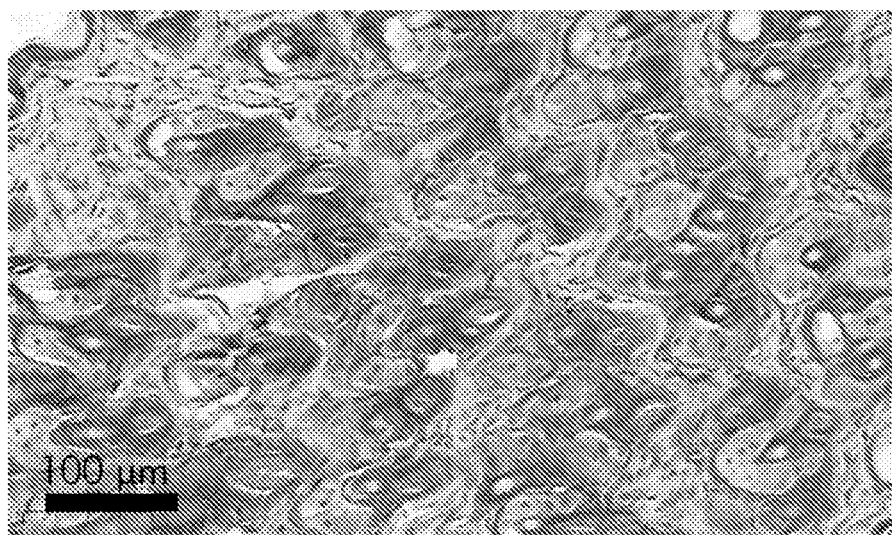
Figure 9C:
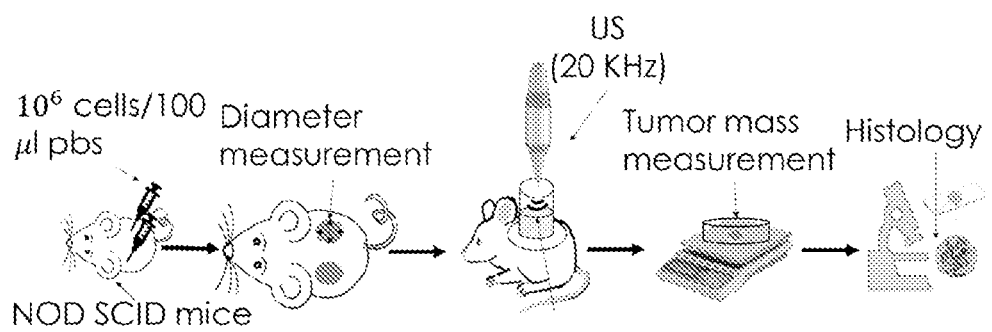
Figure 9D:
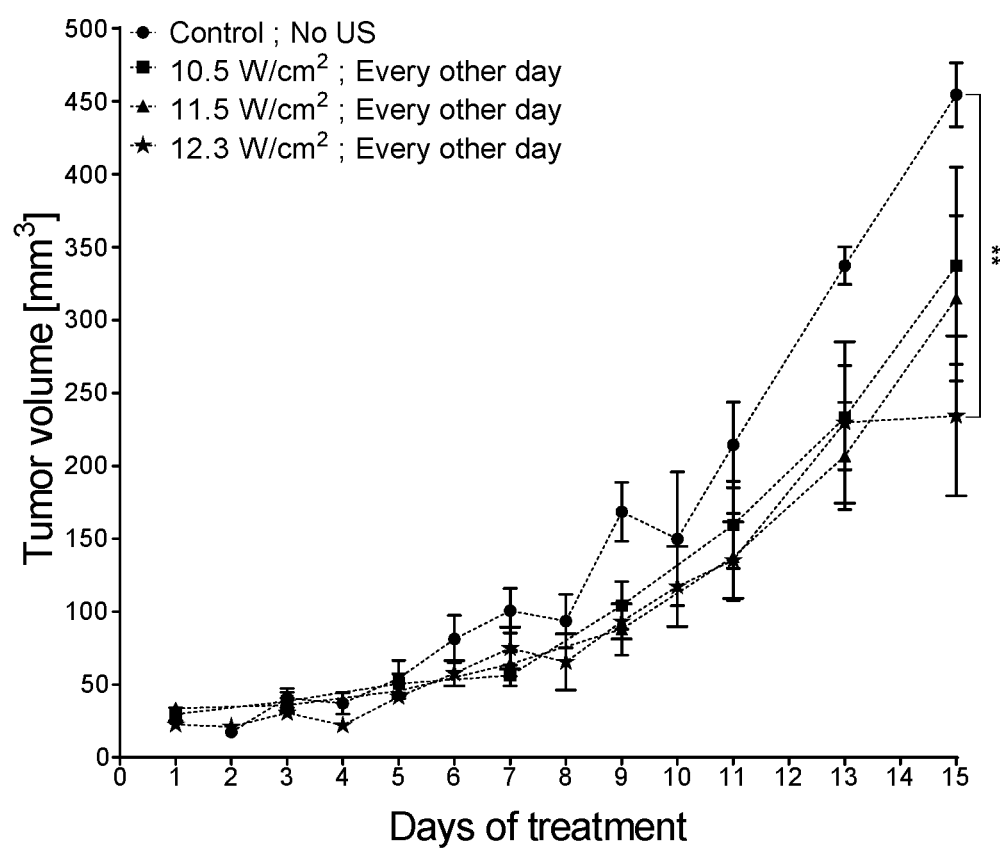
Figure 9E:
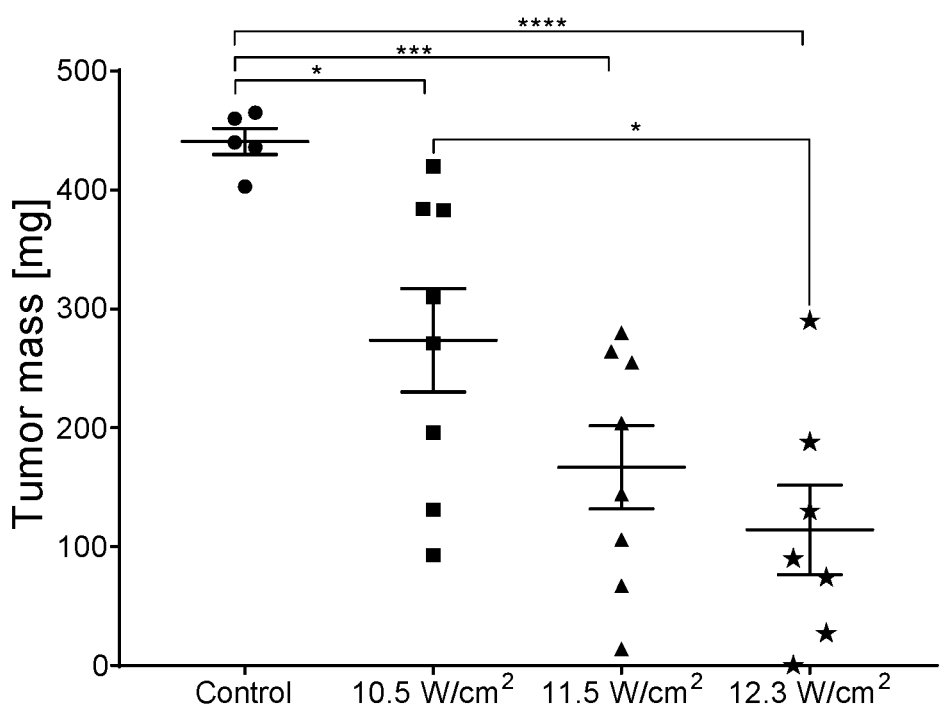
Figure 9F:
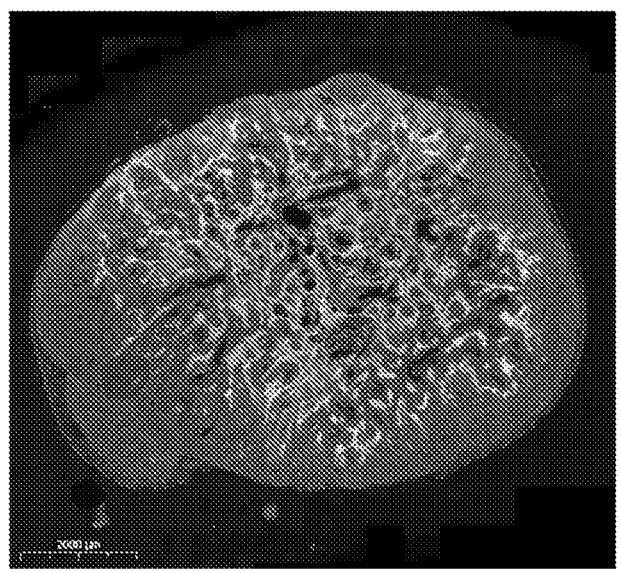
Figure 9G:
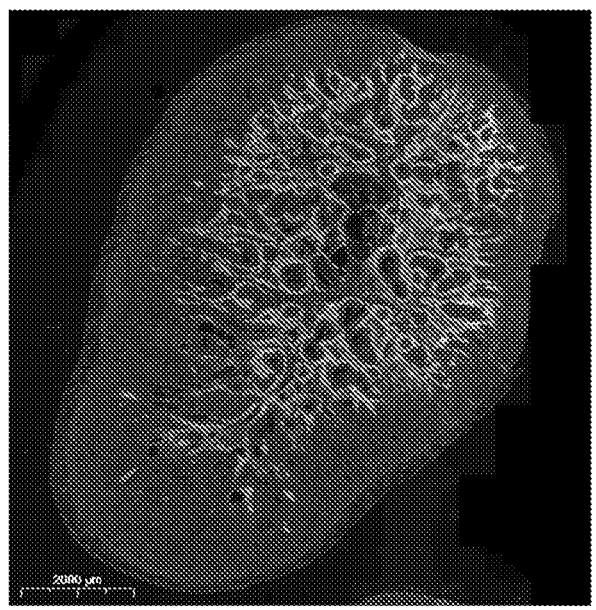
Figure 9H:
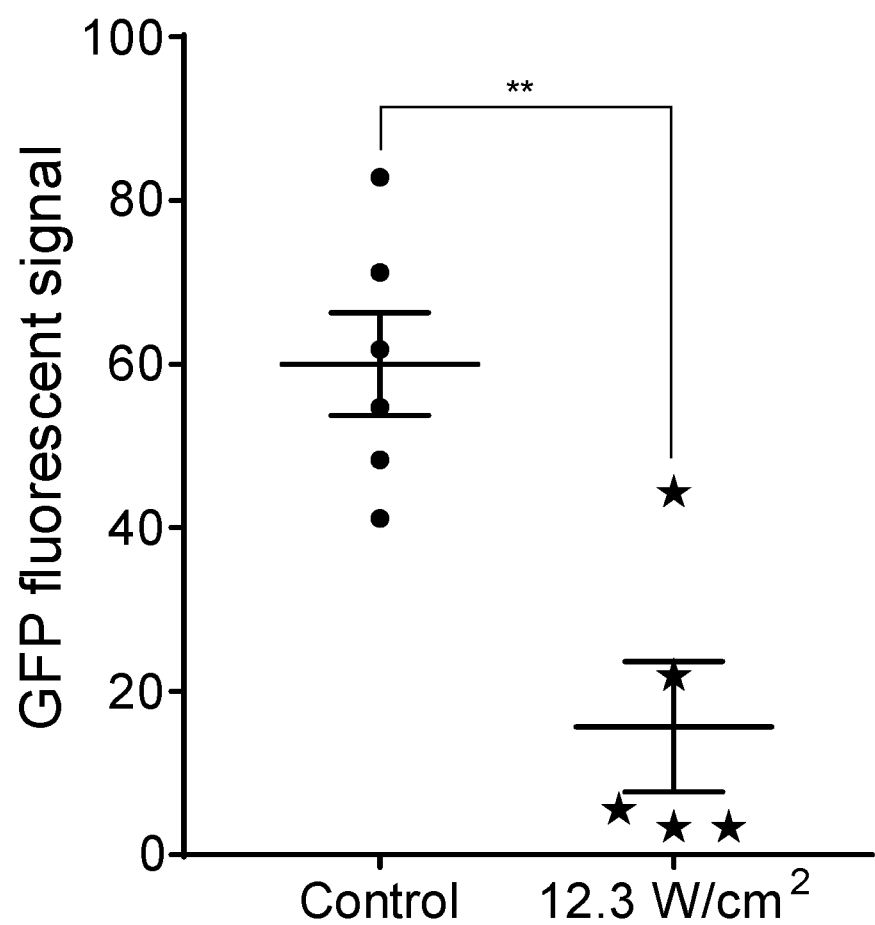

FIG. 9A-FIG. 9G: FIG. 9A is a visual view (photograph) of NOD/SCID mice skin after US exposure; FIG. 9B is a micrograph of Hematoxylin and eosin stain (H&E) histological analysis of mouse skin exposed to US (3 min operation time at intensity of 12.3 W/(cm²) and 50% duty cycle). FIG. 9C is a schematic presentation of the in vivo procedure, comprising injection of the tumor cells in PBS; tumor volume calculation based on diameter measurement US (using caliper); application; tumor mass measurement; and finally H&E staining and pathology. FIG. 9D is a graph showing tumor volume throughout US treatment using three different US intensities for 1 min at 50% duty cycle: Tumor volume change along 15 days of ultrasound intermediate treatment (every other day). FIG. 9E is a bar graph showing HNSCC tumor mass measurements in cells, 15 days after the first US exposure; Florescent scanning of Cal33-GFP histological sections of the affected cells in which the GFP was labeled in green and the nucleus was labeled in blue are shown in FIG. 9F (control) and in FIG. 9G (US exposure at an intensity of 12.3 W/cm²). FIG. 9H is a quantification of the GFP fluorescent signal obtained in FIG. 9F (control) and in FIG. 9G (12.3 W/cm²)

Figure 10A:
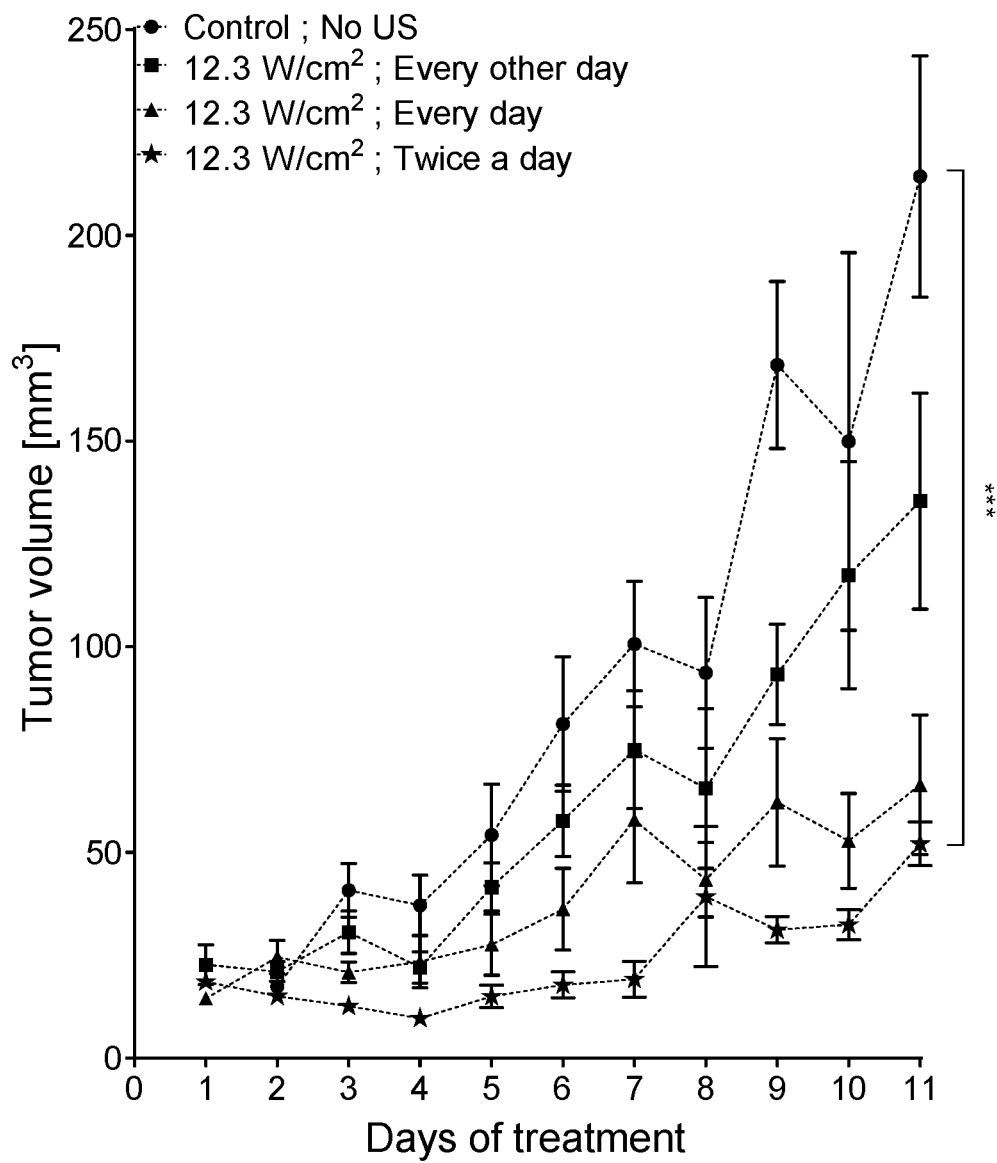
Figure 10B:
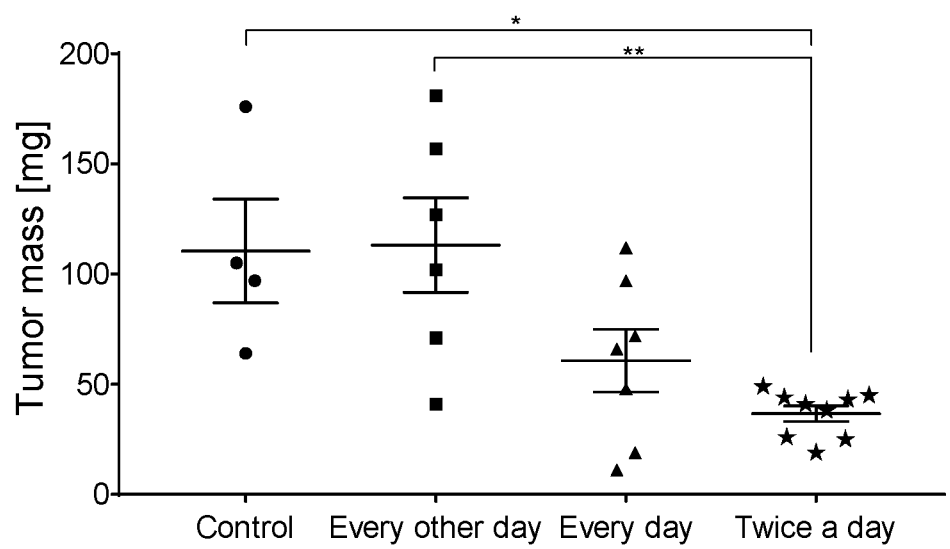

FIG. 10A-FIG. 10B: FIG. 10A is a graph showing the effect of US Repetitions on HNSCC Tumors growth: tumor volume change along 11 days of treatment with US (1 min operation time at intensity of 12.3 W/(cm²) and 50% duty cycle) for a different exposure repetitions: control-no US exposure; US exposure every other day; US exposure once a day; US exposure twice a day. FIG. 10B is a graph showing tumor mass measurements, 11 days after the first US exposure. Statistical significance was calculated using one-way ANOVA test, with post-hoc Sidak's multiple comparisons test*p<0.05, p<0.01, *p<0.001, ****p<0.0001.

Figure 11A:
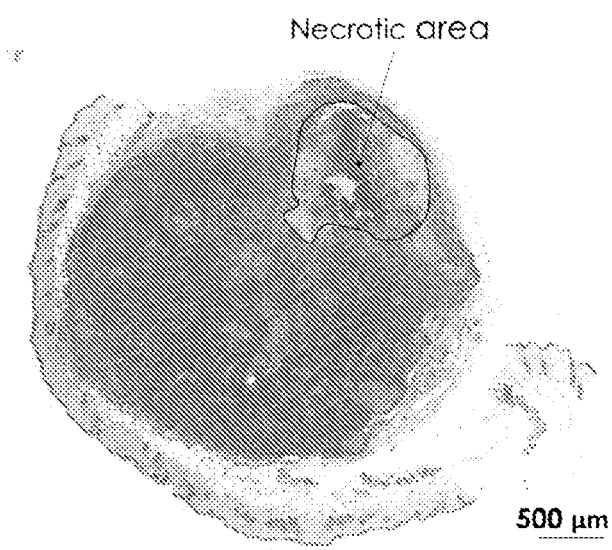
Figure 11B:
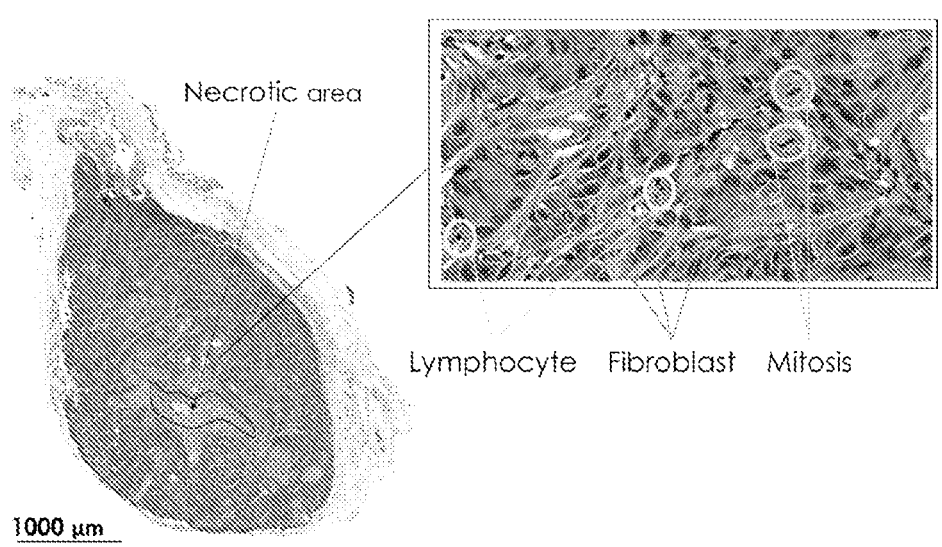
Figure 11C:
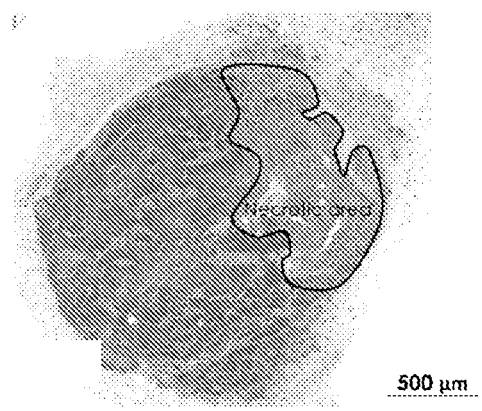
Figure 11D:
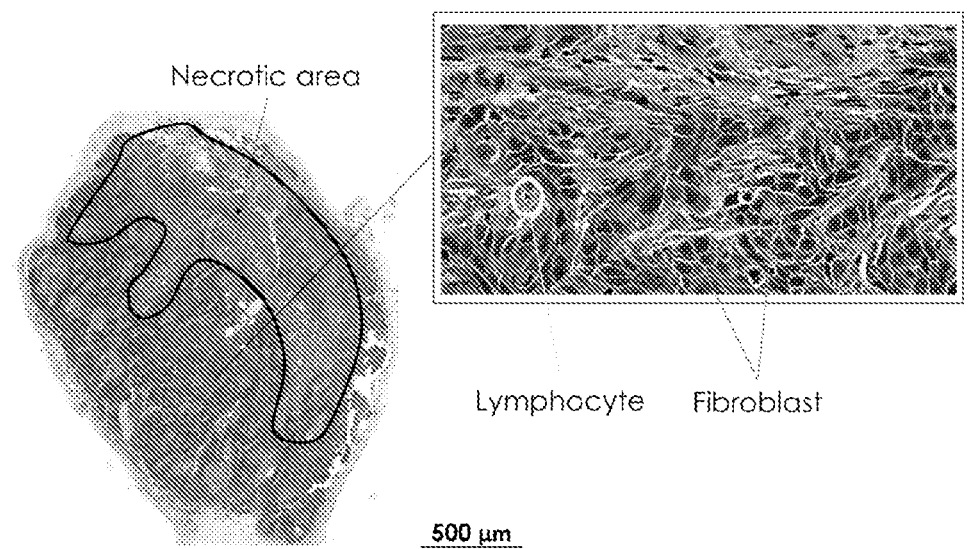

FIG. 11A-FIG. 11D: Representative images of H&E histological section of Cal33 tumor and an example of the morphologic analysis that was performed. FIG. 11A is an image of H&E histological section of untreated HNSCC tumor (control) 48 hours after the first treatment of the corresponding treated cells; FIG. 11B is an image of H&E histological section of untreated HNSCC tumor 11 days after the first treatment of the corresponding treated cells; The right panel is an enlargement of a section, in which lymphocytes, fibroblasts and mitosis are shown. FIG. 11C is an image of H&E histological section of US treated (1 min operation time at intensity of 12.3 W/(cm²) and 50% duty cycle) HNSCC tumor twice a day 48 hours after the first treatment. In FIG. 11D, H&E histological section of HNSCC tumor treated as detailed in FIG. 11C, 11 days after first US application is shown (the right panel provides an enlargement of the section, in which lymphocytes and fibroblasts are shown). The area of necrosis was marked and the area of necrosis (AON) calculated, after which the percentage out of the entire tumor volume was calculated (AON %). Morphologic characteristics of necrosis consisted of areas of mitosis, lymphocytes, and fibroblasts.

Figure 12A:
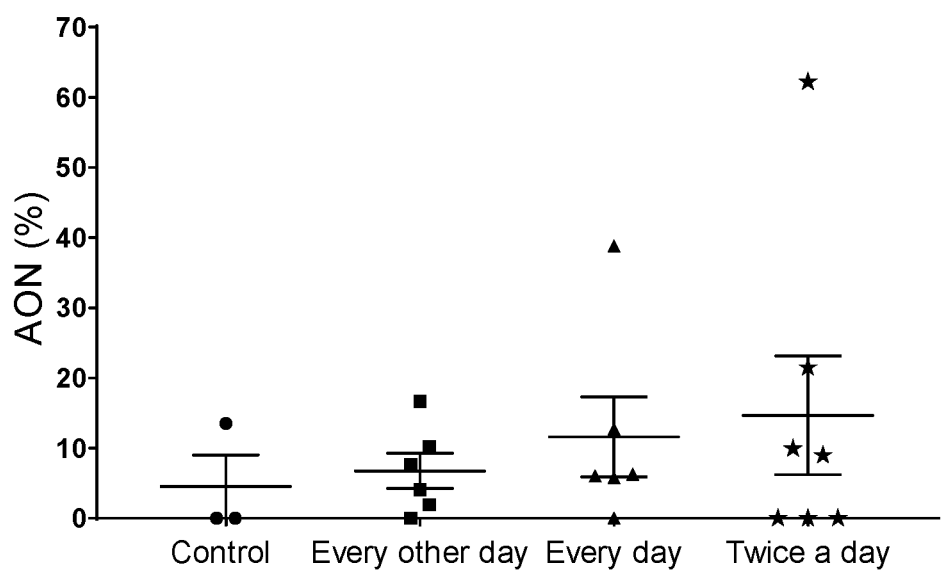
Figure 12B:
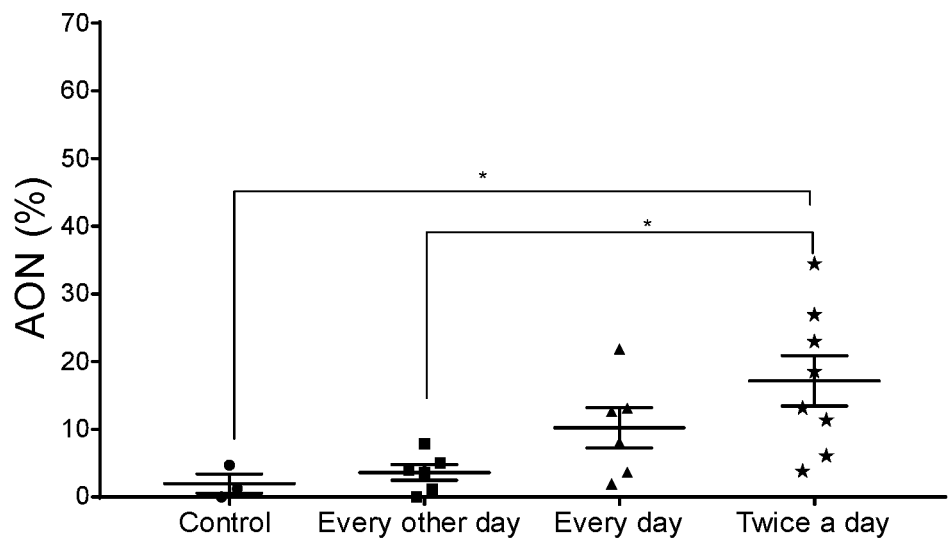
Figure 12C:
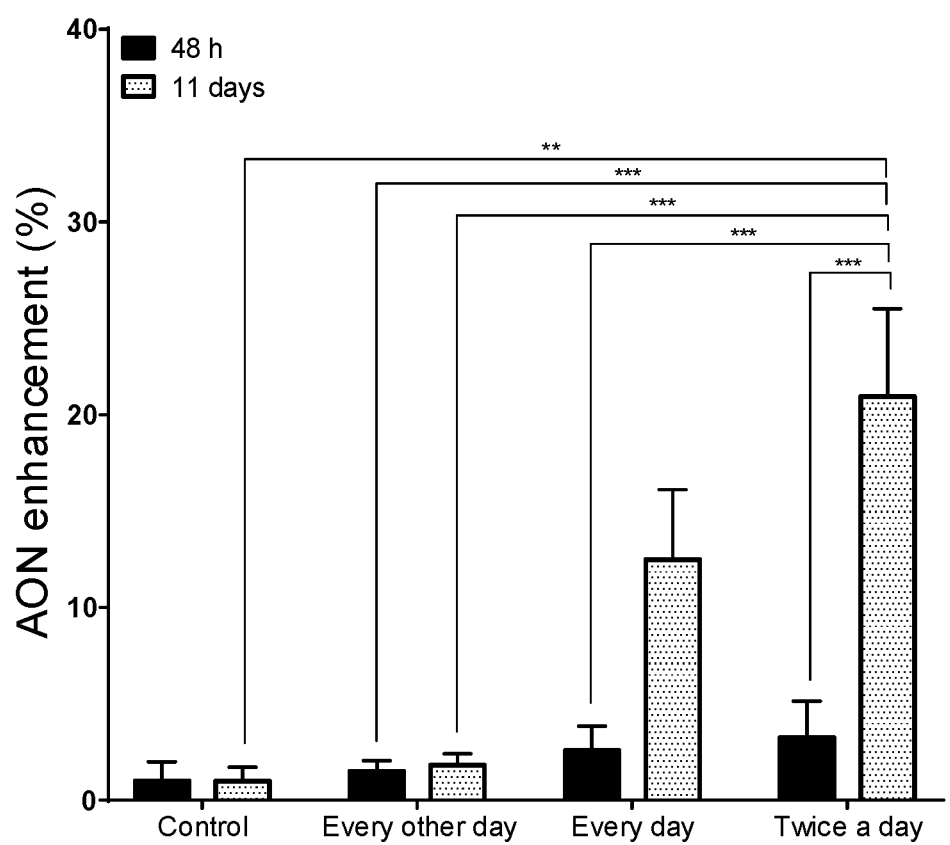

FIG. 12A-FIG. 12C: US treatment-induced necrosis in tumor. FIG. 12A is a graph showing the AON percentage (as a result of US treatment at 1 min operation time at an intensity of 12.3 W/(cm²) and 50% duty cycle) per tumor for all of the experimental groups, using ImageJ (open source software based on NIH Image™, currently available at https://imagej.net/ImageJ) and case viewer programs (*p<0.05) 48 hours after the first treatment. The AON percentage 11 days after the first US application in the experimental groups presented in FIG. 12A is graphically shown in FIG. 12B. FIG. 12C is a graph showing tumor kinetics (enhancement of necrotic area) 11 days and 48 hours following various treatment regimens (control, every other day, every day and twice a day treatments). p<0.01, *p<0.001, ****p<0.0001.

DETAILED DESCRIPTION OF THE INVENTION

It has now been found by the inventors of the present invention that non-invasively exposing cancerous and metastatic cells to ultrasound at optimal low intensities results in higher mortality of cancerous cells and metastatic cells, as compared to normal and/or healthy cells. This enables the selective non-invasive treatment of cancer and other hyperproliferative diseases and disorders or tumors caused therefrom, without harming healthy tissue or cells, and while using solely ultrasound at low intensities.

Thus, according to one aspect of the invention, there is now provided a method of treating a subject suffering from a disease or a disorder associated with hyperproliferating cells, this method comprising non-invasively administering to the subject ultrasound at a low intensity, in a dose effective to prevent the growth of the hyperproliferating cells or to eliminate the hyperproliferating cells in the subject, while substantially not affecting normal cells of the subject.

Furthermore, the difference in selectivity of the present method implies that the cancerous cells do not need to be identified or marked in any way, since the method of the present invention will only affect the cancerous cells, and will not harm healthy cells. Therefore, provided herein is a method utilizing the application of ultrasound at low the intensities for non-invasive treatment of hyperproliferative diseases and disorders or tumors caused therefrom, without combining it with other diagnostic tools or markers. Alternatively, as described in greater detail below, it may be advantageous to determine an elasticity parameter of the cancer cells, e.g. on cell samples available from routine biopsies, and optionally also of vicinal healthy cells (e.g. stromal cells), by methods such as confocal microscopy or atomic force spectroscopy, as generally described herein. This is in order to adapt and/or optimize the intensity and/or the regimen of the insonation by US.

This is advantageous over, for example, the method disclosed in US Patent Application No. 2013/0131432 which will not be able to differentiate and/or affect a cancerous cell if it has the same size of a normal cell, at a given resonance frequency, and which used frequencies (16 MHz and higher) that may be considered exceptionally high in therapeutic applications of ultrasound.

As noted above, the method of the present invention can be based solely on the selectivity of the chosen ultrasound intensity, and does not need any additional methods or steps to identify or target the proliferative cells.

Thus, according to one preferred embodiment of the invention, the method provided herein avoids the use of any additional step for identifying or targeting the hyperproliferating cells.

Alternatively, the method of the present invention may be combined with other diagnostic tools or markers, such as those determining the mechanical properties of the affected cells, as detailed below. It has been unexpectedly found by the present inventors that a low mechanical strength of cancerous cells may be indicative of the susceptibility to US treatment. Thus, provided herein is method according to one aspect of the invention, comprising non-invasively administering to the subject ultrasound at a low intensity, in a dose effective to prevent the growth of the hyperproliferating cells or to eliminate the hyperproliferating cells in the subject, while substantially not affecting normal cells of the subject, wherein the method comprises determining an elasticity parameter of the cancer cells, e.g. in a sample obtained from the subject.

As used herein, the term "treating" or "treatment", as is well understood in the art, refers to an approach for obtaining beneficial or desired results, including clinical results. These include, but are not limited to, curing, alleviation or amelioration of one or more symptoms or conditions, diminishment of extent of disease, stabilizing (i.e. not worsening) state of disease (e.g. maintaining a patient in remission), preventing spread of disease, delay or slowing of disease progression, amelioration or palliation of the disease state, diminishment of the reoccurrence of disease, and remission (whether partial or total), whether detectable or undetectable. The term "Treating" and "Treatment" can also mean prolonging survival as compared to expected survival if not receiving treatment. The term "treating" also includes inhibiting future onset or development of the disease.

As used herein, the term "subject" includes all members of the animal kingdom including mammals, and more preferably refers to humans. Optionally, the term "subject" includes mammals that have been diagnosed with cancer or are i remission.

As used herein, the term "disease" refers to any disease, disorder, condition or to any pathological or undesired condition, state, syndrome, or to any physical, morphological or physiological abnormality.

As used herein, the term "disease or a disorder associated with hyperproliferating cells" used interchangeably with the term "hyperproliferative diseases and disorders", includes diseases which associated are with an abnormally proliferating cell population, and in particular diseases which are associated with an abnormally hyperproliferating cell population, such as tumors and/or cancers. Determining the proliferative state of cells and diagnosis of hyperproliferating cells and a disease or disorder associated therewith are performed by a skilled physician.

In accordance with another embodiment disclosed herein is a method of treating a subject suffering from a disease or a disorder associated with abnormal tissue growth comprising administering to the subject ultrasound at low intensity of up to 100 W/cm$^2$, and, depending on the US frequency, even as low as 12.5 W/cm$^2$, or even 0.5 W/cm$^2$, and over a period of time effective to inhibit or prevent the abnormal tissue growth in the subject.

In some embodiments of the method provided herein the subject is suffering from a tumor or a neoplasm. In various embodiments of the method provided herein the tumor is selected from a pre-malignant tumor and a malignant tumor.

In some preferred embodiments of the method provided herein the abnormal tissue growth is malignant.

In another preferred embodiments of the method provided herein the disease or disorder is cancer. Preferably, the tumor is selected from the group consisting of a pre-malignant tumor and a malignant tumor.

In accordance with an embodiment provided herein is a method of treating a subject suffering from metastasis comprising administering to the subject ultrasound at a low intensity, in a dose effective to inhibit or prevent the growth and/or spread of metastasis in the subject.

The term "cancer" as used herein refers to a broad group of various diseases involving unregulated cell growth. In cancer, cells divide and grow uncontrollably, forming malignant tumors, and invade nearby parts of the body. The cancer may also spread to more distant parts of the body through the lymphatic system or bloodstream.

As used herein, the term "tumor" refers to a malignant tissue comprising transformed cells (also referred to herein as "hyperproliferating cells") that grow uncontrollably. Non-limiting example of cancers and tumors include leukemias, lymphomas, myelomas, and the like; and solid tumors such as, for example, sarcomas and carcinomas, chordoma, endotheliosarcoma, lymphangiosarcoma, Ewing's tumor, brain tumor, skin tumor, breast tumor, colon carcinoma, pancreatic cancer, breast cancer, ovarian cancer, prostate cancer, Wilms' tumor, cervical cancer, testicular tumor, glioma, astrocytoma, medulloblastoma, craniopharyngioma, ependymoma, pinealoma, melanoma, neuroblastoma, and retinoblastoma.

Some Examples of tumors and/or cancers include, but are not limited to, metastatic cancers, cancers of the colon, uterine cervix, breast, pancreas, liver, lung, brain, retinoblastoma, skin (e.g., melanoma) or epidermal [e.g., squamous-cell carcinoma (SCC), basal cell carcinoma (BCC) and a non-melanoma skin cancer (NMSC)], lymphoma (e.g., Burkitt's lymphoma, non-Hodgkin's lymphoma) as well as various leukemias such as acute lymphoblastic leukemia (ALL), acute myeloid leukemias (AML) and chronic myeloid leukemia (CML).

In particular embodiments the methods described herein are applicable to cancers of superficial organs, for example head and neck cancers and any type of skin cancers.

In certain embodiments, the term "metastatic tumor", used interchangeably with the term "metastatic cancer", refers to a tumor that is capable of metastasizing, but has not yet metastasized to tissues or organs elsewhere in the body. In certain embodiments, the term metastatic tumor refers to a tumor that has metastasized to tissues or organs elsewhere in the body. In certain embodiments, metastatic tumors are comprised of metastatic tumor cells.

Thus, according to one preferred embodiment of the invention, the disease or the disorder is cancer, more preferably a metastatic cancer.

Other diseases with hyperproliferating cell population which can be treated by the method of the present invention include, but are not limited to, skin disorders, inflammatory proliferative disorders such as autoimmune proliferative disorders [e.g., rheumatoid arthritis (proliferative synovitis) and viral (e.g., EBV)—induced lymphoid proliferation], psoriasis, proliferative retinitis and ulcerative colitis and the like.

According to one preferred embodiment of the invention, the hyperproliferating cells are selected from the group comprising of cancerous and/or malignant and/or metastatic cells, or any combination thereof.

The term "cancerous cell" refers to a cell that exhibits one or more characteristics or hallmarks of cancer. Such hallmarks of cancer include self-sufficiency in growth signals, insensitivity to growth-inhibitory (antigrowth) signals, evasion of programmed cell death (apoptosis), limitless replicative potential, sustained angiogenesis, and tissue invasion and metastasis.

The term "malignant cell", as used herein, refers to a neoplastic or transformed cell.

The terms "neoplastic" refers to an abnormal mass of tissue as a result of neoplasia. Neoplasia is the abnormal proliferation NOF cells. The growth of neoplastic cells exceeds and is not coordinated with that of the normal tissues around it. The growth persists in the same excessive manner even after cessation of the stimuli. Neoplasms may be pre-cancerous or cancerous. In one embodiment, compositions and methods described herein are directed to pre-cancerous or cancerous cells. As used herein the term "Pre-cancerous" refers to an early form of cancer that is defined by the absence of invasion of tumor cells into the surrounding tissue. Pre-cancerous also refers to dysplasia, which is the earliest form of pre-cancerous lesion recognizable in a biopsy by a pathologist.

As used herein, the term "metastatic cell" as used herein is defined as the transfer of cancer cells from one organ or part to another organ or part which is not directly connected with it.

As used herein the term "administering" refers to ultrasonic stimulation of a cell, a tissue or an organ.

In the field of ultrasound treatment, ultrasound at intensities higher than a threshold intensity (depending on the various parameters such as tissue type, coupling medium properties, frequency, organ/tissue temperature and gas content) often cause some form of cavitation and temperature elevation, which in turn, causes various kinds of tissue damage not only to the cancerous tissue, but also to all of the neighboring exposed healthy tissue. Therefore the term "threshold intensity" is often referred to as "cavitational threshold intensity".

In contrast, as shown in the Examples below, the inventors have now shown that using ultrasound intensities lower than the cavitational threshold intensity, for example of 12.5 W/cm$^2$ and below, even at a frequency of 20 kHz, can be sufficient to selectively affect the viability of cancerous or malignant cells, as opposed to healthy and/or normal cells.

Furthermore, as exemplified in Examples 6 and 7 below, in mice, low frequency US treatment inhibited tumor growth, the repetition of US treatment was associated with an enhanced reduction in tumor's volume without causing damage to healthy skin tissue. Histopathology analysis of tumors indicated that US-induced focal necrosis in the site of treatment. Altogether, these results support US as a non-invasive selective cancer treatment.

As used herein, the term "normal cell" used interchangeably with the term "healthy cell" describes a cell which does not exhibit uncontrolled cell growth and the ability to metastasize. The term "normal cell", as used herein, also encompassed the terms "benign cell" and "non-malignant cell".

Thus, according to one preferred embodiment of the invention, there is now provided a method of treating a subject suffering from a disease or a disorder associated with hyperproliferating cells, the method comprising non-invasively administering to the subject ultrasound at a low intensity in a dose effective to selectively prevent the growth of the hyperproliferating cells or to eliminate the hyperproliferating cells in the subject, while substantially not affecting the cell viability of normal cells of the subject, wherein the low intensity is pre-determined to be lower than a cavitational threshold intensity for a selected frequency.

The ultrasound treatment regime, also referred to as an ultrasound dose or "dose", includes a series of ultrasound parameters, including, but not limited to, ultrasound energy dose, ultrasound frequency, ultrasound intensity, duty cycle, and treatment time.

These specific ultrasound working parameters (ultrasound dose) vary and may depend on a variety of factors, including the age, body weight, general health and sex of the individual being treated; other therapies and drugs that have been administered previously or in combination with the ultrasound therapy; and the type and severity of the particular condition (e.g. malignant disease) undergoing therapy.

Additional ultrasound working parameters include, but are not limited to, distance of transducer, area of transducer and additional parameters as detailed below, and as are known to a person skilled in the art.

While the exact intensity is determined by a person skilled in the art, according to all of these factors, the term "low intensity" refers to an intensity that is lower than the cavitational threshold intensity, and which selectively prevents the growth of the hyperproliferating cells or eliminates the hyperproliferating cells in the subject, while keeping normal cells substantially unaffected.

The terms "selectively prevent" and the term "substantially unaffected" as used herein, both refer to a selectivity in the effect of the ultrasound intensity on cell viability, between cancerous and non-cancerous cells.

According to one preferred embodiment, the method of the present invention results in a cell viability of less than 40% for hyperproliferating cells and, and a cell viability of more than 60% for normal cells.

According to another preferred embodiment, the method of the present invention results in a cell viability of less than 20% for hyperproliferating cells and a cell viability of more than 70% for normal cells.

Thus, cell viabilities of 60% or higher for normal cells, simultaneously reflect they are substantially unaffected by the method of the present invention.

This is quite in contrast to the use of HIFU on its own, which is just as harmful to normal tissue as it is to cancerous tissue. Hence, the selectivity of the HIFU method is restricted only by the focal area of the instrument, and not as a result of a different effect on healthy and cancerous cells/tissues, as in the present application. Therefore, while HIFU on its own cannot be used to treat cancer in sensitive or small areas, due to possible damage to adjacent tissues, its use in combination with the presently taught method can largely broaden the scope of use of HIFU and enable using it in treatments of cancer in areas that have not been treated by HIFU before and also be beneficial to larger tumors since it may speed the process and can be used more "freely" than in the current methods used today.

As noted hereinabove, the treatment regime includes, but is not limited to, intensity, frequency, duty cycle, time of the treatment, distance of transducer from the subject, and the area of the transducer.

Intensity

The term "ultrasound intensity" is used interchangeably with the terms "intensity", "power output", "power density", "power surface density", "acoustic output", and "spatial average intensity", measured in Watts per unit area, usually in Watt/cm$^2$ (W/cm$^2$) units.

While in HIFU applications, on its own, the ultrasound intensity is usually above 100 W (since HIFU is not relative to an area, the units are in watts) and even up to 10,000 W, the present invention shows that much lower intensities can be used, as long as they are lower than the cavitational threshold intensity, and are able to selectively differentiate between hyperproliferating cells and normal cells.

For example, for a frequency of 20 kHz, it was shown that the ultrasound intensities can be lower than about 12-15 W/cm$^2$. It is known that the cavitation intensity threshold is dependent on the US frequency, and at the low-frequency ultrasound the cavitational threshold is the lowest.

It should be noted that a number of intensities, as described herein, were found to be effective for a frequency of 20 kHz, but for higher frequencies, such as up to 10 MHZ, the intensity can be higher, for example up to 100 W/cm$^2$. These intensities were found to be both lower than the cavitational threshold intensity, and able to differentiate between hyperproliferating cells and normal cells.

Thus, according to one embodiment of the invention, this method is characterized in applying the ultrasound at an intensity of up to 15 W/cm$^2$ at a frequency of 20 kHz.

It has also been shown that the ultrasound intensity can be as low as 13.6 W/cm$^2$, e.g. 12.3 W/cm$^2$, lower than 12 W/cm$^2$ (e.g. 11.5 W/cm$^2$, 10.5 W/cm$^2$ or 10 W/cm$^2$), and even lower than 9 W/cm$^2$, and even lower than 6 W/cm$^2$; for example 4.15 W/cm$^2$, 4.38 W/cm$^2$ and 5.09 W/cm$^2$, while maintaining its selectivity on cell viability between cancerous and non-cancerous cells.

Thus, according to another preferred embodiment of the invention, the method is characterized in applying the ultrasound at an intensity of up to 6 W/cm$^2$. Alternatively, according to other preferred embodiments of the invention, the method is characterized in applying the ultrasound at an intensity of up to 10.5 W/cm$^2$, or up to 11.5 W/cm$^2$, or up to 12.3 W/cm$^2$.

According to another embodiment of the invention, the method as herein defined is characterized by applying the ultrasound at an intensity of up to 100 W/cm$^2$ at a frequency of up to 10 MHZ.

The process for finding the optimal ultrasound intensity, for a given ultrasound frequency, would generally proceed as follows: First, the cavitational threshold intensity should be determined for the specific application and conditions.

The term "cavitational threshold intensity" as used herein refers to the minimum intensity required to achieve the cavitation phenomenon. Namely, the minimum intensity at which the undesirable bubble formation occurs.

This value can be determined in a number of ways known to a person skilled in the art, and may be determined by visual inspection of the cells, and determination of the intensity beyond which a visual collapse of cells and/or injury to an organ occur.

Additionally, as detailed in Azagury, A. et al. incorporated herein by reference (Ultrasound in Med. & Biol., Vol. 42, No. 7, pp. 1560-1567, 2016), the US parameters may be calculated with reference to the low-frequency mechanical index (termed "MI$_{LF}$"). Thus, the intensities that were used in the in vitro experiments described herein below, e.g. 4.15, 4.38 and 5.09 W/cm$^2$ were selected to fall below the cavitational threshold based on the adjusted mechanical index for low-frequency US (20-500 kHz) which was suggested by Ahmadi, F. et al. (Progress in Biophysics and Molecular Biology Vol. 108, No. 3, pp. 119-138, 2012).

Based on Ahmadi, F. et al., the adjusted mechanical index for low-frequency US is calculated as follows:

$$MI_{LF} = \frac{P - P_0}{\sqrt{f}}$$

in which P is the US amplitude pressure, P$_0$ (MPa) is the ambient pressure and f (MHz) is the frequency. When the frequencies are outside the low-frequency range, the P$_0$ value becomes negligible and is not taken into account. The US pressure is readily calculated from the intensity as the square root of the product of intensity, medium density, and the speed of sound in the medium. The calculated MI$_{LF}$ values, assuming the unity density for water and 1.52×10$^5$ cm/s sound velocity, for some of the intensities used in vitro (below) were 1.07, 1.11 and 1.25 for 4.15, 4.38 and 5.09 W/cm$^2$ respectively. According to the FDA, for the frequencies between 1-15 MHz, the MI$_{LF}$ threshold limit for US inertial cavitation is 1.9.

However, as demonstrated in the examples below, the elasticity of the cancerous cells is significantly lower than that of the normal tissue cells. Without being bound by a particular theory, it is currently believed that as the ultrasound waves travel through a tissue containing cancer cells, they encounter heterogeneous "organ", a plurality of alternating discrete domains (i.e., cells and cell aggregates at different stages, and normal tissue cells) with significantly different elasticity, and thus the velocity at which these waves cross the tissue will change according to the nature of these domains. As the thickness s of these domains is much lower than the wavelength of the ultrasound even at 200 kHz, some degree of scattering may occur in the cancer-affected tissue, which in turn reduces the ultrasound focal pressure. It is therefore assumed that the apparent mechanical indices, i.e. indices calculated for normal homogeneous tissue, of higher than 1.9 may still be safe to the cancer-containing tissue. Thus, in some embodiments, the ultrasound applicable according to the invention may have a low-frequency mechanical index lower than 2.0, or lower than 2.1, or lower than 2.2, or lower than 2.3, or lower than 2.4, or even lower than 2.5. As demonstrated in the examples below, the intensities of 10.5 W/cm2, 11.5 W/cm2, and 12.3 W/cm2, produced the MI of 2.11, 2.24, and 2.34 respectively.

Once the threshold intensity is determined or calculated, it would serve as the maximal intensity to be tested for that frequency. As shown in the Examples section below, for both the in vitro and in vivo experiments, the intensity was easily set below the cavitational threshold intensity.

Then, approximately a tenth of the determined cavitational threshold intensity would be assessed for its effect on "healthy" and cancerous cells' viability. The intensity would be increased stepwise and the optimal intensity would be the one yielding the highest difference in cells viability of healthy and cancerous cells. Alternatively, the intensity may be adjusted taking into account the measurement of the elasticity of the cancer cells, which may be determined as described below.

In the case of low frequencies, such as the 20 KHz frequency set in the Examples below, the stepwise increase in intensity may be difficult to demonstrate and adjust, and a higher flexibility in the setting of the intensity is achieved for higher frequencies.

Finally, as exemplified in Examples 1-3 below, the duration and duty cycle of the ultrasound application would be adjusted in order to control and fine-tune the application to achieve maximal difference in the response of the hyperproliferative cells and the normal cells.

As can be equally well seen in the further examples 4 and 5, the lower the cancer cell elasticity is, particularly in reference to the vicinal healthy cells, the higher is the sensitivity of the cells to the insonation. Thus, once the elasticity parameter is determined, insonation parameters may be adjusted to maximize the safety of the application.

Generally, the maximum energy dose may be defined. The maximum energy dose will be dependent on the size of the area to be insonated, on the progression stage of the disease, the gas and water contents in the surrounding tissues, and other related parameters. The maximum energy dose can be determined experimentally, e.g. in preclinical studies, as the dose that causes no irreversible damage to the healthy tissues after a single application. As described below, it is usual that the ultrasound be administered on multiple occasions, to increase the efficacy of the treatment by repeated exposures. The maximum energy dose may thus be safety-factored for multiple exposures, e.g. according to the clinical state of the patient. The usual safety factor to be applied will be e.g. between 3 and 20, e.g. between 5 and 10, and may be dependent on the healthy tissue (e.g. skin) health and thickness, area of insonation, part of the body, and other clinical considerations. As demonstrated in the examples below, the energy doses between about 3 and about 15 kJ were applied to the affected regions with initial tumour volumes of as little as ca. 25 mm$^3$. The energy doses for multiple exposures may be even higher, e.g. between 5 and 20 kJ, or between 7 and 30 kJ.

Once the energy dose for the treatment has been selected, the insonation parameters, such as the intensity, the duty cycle, and the insonation time will be readily determined, as follows. The maximum intensity will be selected such that the apparent mechanical index of the insonation is between 1.9 and 2.5. The duty cycle is usually selected below 100%, to prevent overheating of the tissues and to minimize the thermal effects. Usually the duty cycle will be between 30 and 60%; however when a sensitive tissue is involved, it can be selected between 10 and 50%. The insonation duration will be readily calculated with these parameters selected, as the energy dose is the product of the intensity, insonation area, the duty cycle, and the duration of insonation.

With the maximal intensity selected based on the desired mechanical index, e.g. as 13.6 W/cm$^2$ for MI of 2.5 at 20 KHz in aqueous medium, and other parameters selected based on the energy dose, the treatment may be delivered to the patient in need thereof. However, if the elasticities' ratio between the cancer cells and the normal tissue cells of the patient has been established, the intensity of the insonation may be adjusted to lower values. For example, if the ratio of elasticities is between 0.01 and 0.15, a fraction of maximum intensity may be selected for administering at a specific insonation period, which may be between 1 and 40% of the determined maximum intensity. If the ratio of elasticities is between 0.15 and 0.35, then the fraction of the maximum intensity for administering at a specific insonation period may be between 10 and 80%. If the ratio of elasticities is between 0.35 and 0.7, the fraction of maximum intensity for administering at a specific insonation period may be between 25 and 100%.

Thus, according to another preferred embodiment of the invention, there is provided a method of treating a subject suffering from a disease or a disorder associated with hyperproliferating cells, the method comprising non-invasively administering to the subject ultrasound at a low intensity, in a dose effective to selectively prevent the growth of the hyperproliferating cells or to eliminate the hyperproliferating cells in the subject, while substantially not affecting the cell viability of normal cells of the subject, wherein this intensity is pre-determined by:

a. Determining the cavitational threshold intensity for a selected frequency, thereby setting a maximal intensity for the frequency;
b. Setting an intensity of a tenth of the maximal intensity and measuring its effect on the cell viability of both normal cells and hyperproliferating cells;
c. Stepwise increasing the intensity to obtain an optimal intensity exhibiting the highest difference in cell viability between the normal cells and the hyperproliferating cells; and
d. Determining the duration and duty cycle of the ultrasound application to achieve the highest difference in cell viability between the normal cells and the hyperproliferating cells.

In some preferred embodiments, provided herein a method of treating a subject suffering from a disease or a disorder associated with hyperproliferating cells. The method comprises non-invasively irradiating a tissue comprising said hyperproliferating cells in said subject with ultrasound. The ultrasound preferably has a frequency between 20 and 200 kHz and is administered at an intensity between 0.5 and 100 W/cm$^2$, provided that the selected intensity is either below the cavitational threshold intensity for said ultrasound frequency, or is characterized by a low-frequency mechanical index below 2.5. Preferably, the method is carried out with said intensity being between 0.5 and 15 W/cm$^2$ at a frequency of 20 kHz. Further preferably, the method is carried out with said intensity is between 0.5 and 6 W/cm$^2$. The irradiating step may comprise applying said ultrasound for at least one application time interval with duration of from 10 seconds to 10 minutes. Additionally, the method may comprise a plurality of irradiating steps, at a regimen frequency of between twice daily to once weekly.

In some preferred embodiments, the disease or disorder is associated with abnormal tissue growth, e.g. said disease or said disorder is cancer. In some embodiments, the cancer is a superficial cancer. Sometimes, the superficial cancer is a metastatic cancer. A specific type of cancer may be a skin cancer, a head and neck cancer, or a breast cancer.

When the method is carried out with the intensity produces a mechanical index lower than 2.5, it may comprise a further step, a step of evaluating the mechanical properties of said hyperproliferating cells, prior to said irradiating step, and adjusting said intensity based on said evaluating step. The evaluating step may usually comprise obtaining a ratio between the elasticity values of said hyperproliferating cells and healthy tissue cells obtained from the vicinity of said hyperproliferating cells. The elasticity values may usually be obtained by determining the Young's modulus of said hyperproliferating cells in a sample obtained from said subject. The elasticity value of said healthy tissue cells may also be determined based on reference values of Young's modulus characteristic of said healthy tissue cells. In some embodiments, the evaluating step is performed by atomic force microscopy. Alternatively, or additionally, the evaluating step is performed by confocal microscopy with F-actin staining. The adjusting of the intensity step may usually comprise determining a maximal intensity producing a mechanical index of 2.5, and administering the ultrasound at an intensity of between 1 and 40% of the maximum intensity if the ratio of elasticity values is between 0.01 and 0.15, administering ultrasound at an intensity of between 10 and 80% of the maximum intensity if the ratio of elasticity values is between 0.15 and 0.35, and administering ultrasound at an intensity of between 25 and 100% of the maximum intensity if the ratio of elasticity values is between 0.35 and 0.7.

The method may be performed on the tissue that is blood. In these embodiments, the method comprises aseptically obtaining blood from said patient, irradiating said blood with ultrasound, and re-administering said irradiated blood back to said patient.

In further embodiments, provided herein a method for predicting the suitability of a subject suffering from a disease or a disorder associated with hyperproliferating cells to ultrasound treatment by non-invasively irradiating a tissue comprising said hyperproliferating cells, said method comprising the steps of:
  i) determining a cellular elasticity value of said hyperproliferating cells in a sample obtained from said subject;
  ii) determining if the cellular elasticity value of said hyperproliferating cells obtained in step (i) is higher or lower compared to a predetermined standard cellular elasticity value, said predetermined standard elasticity value being characteristic of cells in the surrounding tissue; and
  iii) determining that said patient is suitable to said treatment comprising administering ultrasound, if said cellular elasticity value of said hyperproliferating cells obtained in step (i) is lower than a predetermined standard cellular elasticity value.

Since cavitational threshold intensity increases with ultrasound frequency, the higher the ultrasound frequency, the higher the ultrasound intensities that could be used, thus enabling greater differentiation between the response of healthy and hyperproliferative cells to ultrasound exposure.

Intensity Versus Medium

It should be noted that ultrasound amplitude percentage represents the ultrasound intensity of the instrument. However, it does not necessarily represent the ultrasound intensity that the cells and/or tissue have been exposed to. In the results presented hereinbelow, when exposing the cells/tissue directly to the ultrasound transducer (as was done in the in vivo experiments, Example 3), the ultrasound amplitude percentage of 1 and 2% correlates with exposure intensities of 7.7, 8.2 W/cm$^2$ (respectively). However, in the in vitro experiments (cell lines, Examples 1 and 2), ultrasound amplitude percentage of 18, 2% and 3% correlate with exposure intensities of 4.15 W/cm$^2$, 4.3 W/cm$^2$ and 5.09 W/cm$^2$, respectively. The differences between the exposed intensities derive from the different manner by which the ultrasound was used in the in vitro experiments. Two main parameters affected the reduction in exposed intensity, the distance that the cells were from the transducer used (10 cm vs. 1-2 cm) and the probe size (13 cm vs 1.3 cm).

Frequency

The present invention is based on the selection of an optimal low intensity of ultrasound, at an intensity below the cavitational threshold intensity, that is selective in its effect on the viability of cancerous vs. normal cells, and can be used at virtually any frequency, quite in contrast to methods relying on high intensity of ultrasound, which are mainly based on high frequencies, and whereas there is no selective effect on cancerous cells.

As known to a person skilled in the art, the higher the frequency of the ultrasound, the more intensity that is needed to allow cavitation. Therefore, using low frequencies implies having a low threshold intensity for the formation of cavitation, and using higher frequencies provides a wider range of intensities before risking in the onset of cavitation.

According to one preferred embodiment, the frequency used in the present invention is a low frequency.

As used herein, the term "low frequency" or "LF" refers to frequencies ranging from 20 kHz-200 kHz.

According to another preferred embodiment, the frequency used in the present invention is a medium frequency.

As used herein, the term "medium frequency" or "MF" refers to frequencies ranging from 200 kHz to 1000 kHz (1 MHZ).

According to another preferred embodiment, the frequency used in the present invention is a high frequency.

As used herein, the term "high frequency" or "HF" refers to frequencies higher than 1 MHZ.

It should again be stressed that one advantage of the present invention is that it can be used at any ultrasound frequency, and is based on the selection of an optimal low intensity, as described hereinabove, which shows selectivity in the effect of the ultrasound treatment on cell viability, between cancerous and non-cancerous cells, while being lower than the cavitational threshold intensity.

The present invention preferably uses ultrasound frequencies ranging from 20 kHz to 10 MHZ.

Duty Cycle

While in certain embodiments, the ultrasound can be administered continuously, in other embodiments, the ultrasound can be administered intermittently, using ON/OFF cycles. Those with skill in the art can determine effective ON/OFF cycle times depending, for example on the volume of tumor, type of tumor, and other relevant variables.

Another advantage of the methods and devices provided herein is that the hyperproliferative cells can be effectively treated in short periods of time.

In the case of using ON/OFF cycles, the term "duty cycle" is used to refer to the pulse duration divided by the pulse repetition period. In particular, duty cycle represents the fraction of time that the ultrasound is working, for example, 10% DC means that the ultrasound was on for 1 second and off for 9 seconds (for 1 minute duration, it means that ultrasound was on for 6 seconds and off for 54 seconds at ten seconds intervals).

According to one preferred embodiment of the present invention, the ultrasound is administered at a duty cycle ranging from 10% to 90%.

Additional Ultrasound Treatment Regimen Parameters

Additional ultrasound treatment parameters include: time of application, distance of transducer from the skin of the subject (for non-HIFU applications), size and shape of the transducer, number of treatments, mode of application etc., and a person skilled in the art would easily determine these parameters, depending on the exact need and conditions.

The methods provided herein can be administered as a single treatment or as multiple courses of therapy. Those with skill in the art can determine whether several successive courses of treatment are required, based on the outcomes observed in the previous courses of therapy, until a particular criterion for terminating the patient's therapy is met.

According to one embodiment, the method described herein is characterized in applying the ultrasound at an application time ranging from 10 seconds to 10 minutes. This time refers to each separate treatment, and may be repeated as part of a treatment series. Preferably, the application time of each separate application is up to 1 minute, more preferably about 15 seconds.

The methods provided herein can be used as a monotherapy or in conjunction with other drugs such as, without being limited to, photosensitizers, sonosensitizers and chemotherapeutic agents; and or in conjunction with other therapies such as, without being limited to, anticancer radiotherapy. Such combinations may offer significant advantages, including synergistic activity, in therapy. In addition, such combinations may provide an improved quality of life compared to the quality of life the same patient would experience if they received only the chemotherapeutic agent as therapy. For example, the combined therapy with the low intensity ultrasound described herein may lower the dose of chemotherapeutic agents needed, thereby lessening the side-effects associated with high-dose chemotherapeutic agents (e.g., nausea, vomiting, hair loss, rash, decreased appetite, weight loss, etc.). The combination may also cause reduced tumor burden and the associated adverse events, such as pain, organ dysfunction, weight loss, etc.

The methods provided herein may comprise a preliminary diagnostic step performed on a cell sample obtained from the subject, for assessing the susceptibility of the cancer cells to US treatment, thereby verifying that the cancer patient will benefit from treatment, and for determining which US intensity range would be suitable for treatment.

As exemplified in Examples 4 to 7 below, superficial cancers were the focus of an additional study by the inventors, mainly squamous cell carcinoma of the head and neck (HNSCC). By comparing the mechanical elasticity of the cells by Atomic Force Microscopy (AFM), the average Young's modulus of healthy cells (HaCaT) was found to be significantly higher than cancer superficial cells (namely UM-SCC47, Cal33 and A375).

Furthermore, it is described below that highly aggressive cancer cells such as melanoma cells (A375) and HNSCC cells (Cal33) demonstrated lower Young's modulus than less aggressive cancer cells such as HNSCC cells (UM-SCC47), where non-cancerous cells (HaCaT) demonstrated the highest Young's modulus (as shown in FIG. 7D).

The inventors have further found that cancer cells (Cal33) are much more sensitive to US than healthy cells (HaCaT), in all US energy levels evaluated, and moreover, different cancer cells demonstrated different sensitivity to US at the same US energy level (FIG. 8). The question whether the measured by AFM Young's modulus can predict cells sensitivity to US has been answered by the correlation between Young's modulus and cell viability in vitro. A linear regression with the coefficient $R^2=0.92$ was obtained for the healthy cells and cancerous cells, and for the three cancer's that have been measured, a much more accurate linear regression ($R^2=0.99$) was observed.

In other words, the mechanical elasticity of the cells was found to correlate with the viability of the cells treated by US energy. This positive correlation between cellular rigidity (e.g. Young's modulus, as measured for example by AFM, and evidenced by confocal microscopy with actin staining) and sensitivity to US treatment (cell viability), support that a biomechanical property can predict the cells' sensitivity to US treatment, thereby verifying that the cancer patient will benefit from treatment.

The cancer cells may be obtained from the patient, e.g. by biopsy, as known in the art. The biopsy specimen may be separated to furnish the cancer cells and the vicinal non-cancer cells of the surrounding tissue. The cancer cells may then be proliferated using regular tissue culture techniques, before the measurement of the mechanical properties, e.g. Young's modulus. Additionally, the non-cancerous cells may be separated and proliferated form the biopsy, for the measurement of the mechanical properties.

The Young's modulus of the cancer cells may be readily determined, e.g. by the atomic force microscopy. AFM is a type of scanning probe microscopy, with demonstrated resolution on the order of fractions of a nanometer, more than 1000 times better than the optical diffraction limit. The information is gathered by "feeling" or "touching" the surface with a mechanical probe. Piezoelectric elements that facilitate microscopic but accurate and precise movements on (electronic) command enable precise scanning. The AFM has three major abilities: force measurement, topographic imaging, and manipulation. In force measurement, AFMs can be used to measure the forces between the probe and the sample as a function of their mutual separation. This can be applied to perform force spectroscopy, to measure the mechanical properties of the sample, such as the sample's Young's modulus, a measure of stiffness. The construction of the AFM can be divided into three main parts: (1) a cantilever; (2) a system that detects its deflection; and (3) a system that enables scanning and positioning. The principle of operation is usually independent of the environment surrounding the cantilever (air, vacuum or liquids). The key part of the AFM is the cantilever. Cantilevers are lithographically etched from silicon or silicon nitride, in a form of long and flexible levers (rectangular or triangular ones), with a probing tip mounted at their free ends. The mechanical properties of a cantilever are usually characterized by the corresponding spring constants which, in case of living cell studies, typically ranges from 0.01 to 0.1 N/m. Often, a probing tip has a shape of a four-sided pyramid, but other geometries, such as cones or spheres, are also used in the AFM experiments. The choice of appropriate geometry of the probing cantilever depends on the type of experiments to be carried out. In the case of measurements of living cells, spheres have been also applied, since such geometry of probing tip fulfils better the Hertz model assumptions commonly used in the stiffness parameter value estimation (Young's modulus). The AFM cantilever approaches the cell from a few micrometres above, makes contact with the cell, then indents the cell so that the cantilever deflection reaches a preselected set point and pulls away from the cell. The most frequent way of its detection uses the optical system composed of a laser and a photodetector. During this process, the cantilever deflection is recorded as a function of its location. Before contacting the cell, the cantilever moves in the medium without any apparent deflection. When indenting on the cell, the cantilever bends and the deflection signal increases. The cantilevers are modelled as elastic beams so that their deflection is proportional to the force applied on the cell. By setting the maximum cantilever deflection, the maximum magnitude of force applied to the sample is limited to avoid damage to the cells. Three models have been usually used to derive the Young's modulus of cells: the Sneddon model (cone indenter), the brush models for either conical, or spherical indenters, and the widely used Hertz model (spherical indenter) in which the cell is assumed to be a homogenous material and the cell border is a well-defined interface. To derive the Young's modulus of the cell, the experimental force-indentation curves are fitted with equation:

$$F(i_C) = \frac{16}{9} E \sqrt{\frac{R_{probe} * R_{cell}}{R_{probe} + R_{cell}}} * i^{1.5}$$

Additionally, the elasticity of the cells may be determined indirectly, via F-actin staining of the cells, and measuring the patterns and the intensity of the staining of the cells, e.g. by confocal microscopy. The intensity of the selected color may be measured by the usual confocal microscopy software. Additionally, the continuity of the staining may be determined, e.g. by an algorithm to define the maximum length of stained segments, or by the density of the staining per selected area. The staining and analysis may be performed as generally described below. For example, the cells may be seeded at an appropriate density, and cultured for a time interval to allow attachment of the cells to the material of the culturing vessel, e.g. multi-well glass plate. The cells may then be fixed, e.g. with a formaldehyde compound, washed, and then permeabilized with a surfactant. One useful surfactant may be Triton X-100, e.g. in a concentration of 0.1%. The internal and/or external components of the cells may be stained with fluorescent dyes. Fluorescence images are then obtained using confocal microscopy, with excitation and detection wavelengths or ranges that are suitable to the dyes used.

As detailed above, it may be advantageous to determine the mechanical properties not only of the cancer cells, but also of the non-cancer cells. From these two values a ratio of the elasticity may be readily determined. It may also be possible to determine the ratio directly, e.g. by co-processing the confocal microscopy images of several cells (of both cancer and healthy types) in the F-actin-stained biopsy slide.

As the inventors of the present invention have also demonstrated that various HNSCC cell lines exhibited different sensitivity to the same US application, the above preliminary diagnostic step is considered advantageous for developing a personalized non-invasive therapy for cancer (e.g. superficial cancers) by achieving selective death of cancerous cells.

The association between Young's modulus and the organization and amount of F-actin in cells was previously defined and the cells' mechanical strength was found to correlate with pronounced network of F-actin filaments. Therefore, assessment of F-actin filaments network in cells may be used as an alternative for means evaluating the cells' susceptibility to US treatment.

As shown below, US treatment quantitatively affected superficial tumor progression. These results, together with the results obtained for breast cancer, suggest that the sensitivity to US may be related to a common phenomenon occurring in all cancer cells regardless of their origin and type and hence the potential generality of the present invention for treatment of various cancer types.

In one preferred embodiment of the invention, the method provided herein is non-invasive. As used herein the term "non-invasive" refers to an external application, namely it comprises placing an ultrasonic transducer in contact with the surface of a patient's body or in close proximity to a patient's body, optionally through a coupling medium, that is used to facilitate transmission of the ultrasound energy from the machine head to the tissues.

The term "coupling medium" used in this context includes water, various oils, creams and gels. Ideally, the coupling medium should be relatively fluid so as to fill all available spaces yet relatively viscous so that it stays in place, have an impedance appropriate to the media it connects, and should allow transmission of ultrasound with minimal absorption, attenuation or disturbance. Preferably, the coupling medium is a gel.

Thus, according to one preferred embodiment, the method presented herein comprises placing an ultrasonic transducer in contact with the surface of the subject's body or in close proximity to the subject's body, optionally through a coupling medium. According to one preferred embodiment, in this case, the method described herein is characterized in applying the ultrasound at a transducer distance ranging from 0.5 cm to 5 cm from the subject. Preferably, the transducer distance is up to 4 cm from the subject.

While the person skilled in the art will easily determine the specific ultrasound treatment parameters, according to the exact need, in one preferred embodiment, the method described herein is characterized in applying regular ultrasound (non HIFU) at an intensity of up to 12 W/cm$^2$, a frequency of 20 kHz, a duty cycle ranging from 10% to 90%, at a time of up to 5 minutes, and at a transducer distance ranging from 0.5 cm to 4 cm from the subject.

However, the external non-invasive application of ultrasound also includes the application of High Intensity Focused Ultrasound, such as MRI-guided Focused Ultrasound or HIFU, which is external, yet affects internal organs.

Thus, in another preferred embodiment of the invention, the method provided herein is non-invasive and comprises applying a High Intensity Focused Ultrasonic transducer, optionally guided by an MRI system.

According to a most preferred embodiment, the method presented herein comprises applying a High Intensity Focused Ultrasonic transducer, guided by an MRI system.

Although the external non-invasive treatment is an advantage of the present invention, in another preferred embodiment of the invention, the method provided herein can be interventional and comprises inserting an ultrasonic transducer into a patient's body opening (such as esophagus, rectum, vagina).

Yet further, in certain embodiments the method provided herein can be used for treating hyperfroliferative cells ex vivo. These methods can be performed similar to other ex vivo methods, such as hemodialysis, for example. For example, in certain embodiments the method provided herein comprises extracting a physiological fluid (e.g., blood) from a subject suffering from a hyperproliferative disorder, for example blood cancer. After extraction, the physiological fluid is that the treated with ultrasound at low intensity such hyperproliferative cells have been sufficiently neutralized and/or prevented from growing and/or eliminated; and the treated physiological fluid is administered back to the subject.

Thus, according to one preferred embodiment, the method presented herein comprises applying ultrasound at a low intensity on a physiological fluid extracted from a subject suffering from a hyperproliferative disorder, followed by administering the physiological fluid back to the subject.

As noted hereinabove, one of the unique advantages of the method provided herein lies in the possibility of selectively destructing hyperprolifirating cells (e.g. cancerous cells) and/or tumors (e.g. metastatic cancer tumors) without the need to locate any or all of them. In addition, the method provided herein may be used in conjunction with or incorporated as part of, other treatments, such as for example chemotherapy treatment, to improve treatment effectiveness. Another important advantage of the method as described herein is that it may be applied as early as the cancer is detected, regardless of its stage.

Therefore, according to one preferred embodiment of the invention, the present method avoids the use of any additional step for identifying or targeting the hyperproliferating cells.

In some further embodiments, particularly when a biopsy has been used to confirm the cancer diagnosis, the method may advantageously comprise evaluating the elasticity of the hyperproliferating cells and of their surrounding tissue, and adjusting the intensity of the ultrasound accordingly.

Furthermore, the method as disclosed herein can be used as preventive treatment for patients who overcome cancer, thereby preventing the cancer from recurring or reducing the recurrence of the cancer. Due to the ultrasound low intensities the method as provided herein is not expected to cause any undesirable side effects.

Therefore, according to another embodiment of the present invention, the methods disclosed herein are useful in treating a subject suffering from a disease or a disorder associated with nonmalignant or pre-malignant conditions, involving hyperproliferating cells and/or abnormal tissue growth.

The present disclosure is illustrated in detail below with reference to examples, but is not to be construed as being limited thereto.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Materials

If not otherwise specified below, Glycine (G7126), phosphate-buffered saline (PBS) (P4417), methyl sulfoxide-d6 (DMSO-d6) (547239), and trypan blue (T6146) were purchased from Sigma-Aldrich. Acetone (01030521), and ethanol (05250502) were purchased from Bio-Lab. Microscope slides 76×26 mm were purchased from Thermo Scientific. Dulbecco's modified eagle medium (DMEM) (01-055-1A), RPMI medium 1640 (01-104-1A), minimum essential medium (MEM) (01-045-1A), fetal bovine serum (FBS) (04-121-1A), glutamine (03-020-1B), trypsin (03-052-1A), trypan blue 0.5% (02-102-1B), and penicillin-streptomycin (03-031-1B) were purchased from Biological Industries. Presto Blue™ cell viability reagent (A13261) and Pro-Long® gold antifade reagent with DAPI (P36935) were purchased from Rhenium, septol was purchased from Teva.

Statistical Analysis

Statistical analysis was performed using GraphPad Prism 7.03 software, presented as mean±SEM. All cellular experiments were repeated at least three times. A two-tailed Student's unpaired t-test was performed to compare control vs. treated group. P values of 0.05 (*), 0.01 (), 0.001 (*) and 0.0001 (****) were considered statistically significant. For experiments with more than two groups, two-way ANOVA was used. Sidak's multiple comparisons test was used for post-hoc analysis. For pathological analysis, H&E images were analyzed by Panoramic Viewer Histoquant software (3D Histech), and a one-way ANOVA test was performed to compare control vs. treatment groups.

Example 1: Effect of Ultrasound at Low Intensities on Cancerous Cell and Normal Cells The effect of ultrasound at low intensities was tested on three cell lines: Hela cells which are cancerous cells of ovarian cancer, NCI/ADR-RES (NAR) cells which are cancerous cells of ovarian cancer resistant to chemotherapy and MCF10A cells which are non-cancerous cells. The effects of intensity, duration and duty cycle of ultrasound on cells' mortality were evaluated.

Ultrasound transducer used for all of the experiments was with a frequency of 20 kHz (MISONIX, Model S-4000-010). Cell mortality was determined using a standard viability test using 3-(4,5-Dimethylthiazol-2-yl)-2,5-diphenyltetrazolium bromide (MTT) (available from Sigma, catalogue number M2128, CAS number: 298-93-1) that stains live cells only.

Cell Cultures

NAR cells were cultured in RPMI (Roswell Park Memorial Institute medium, Biological industries, 500 mL, Catalog: 01-109-1A) growth media containing 1% L-glutamine (Biological industries, 03-020-1B), 1% penicillin-streptomycin (Biological industries, Catalog number: 03-031-1B) and 10% fetal bovine serum (FBS, Biological industries, Catalog number: 04-121-1A) at 37° C. and 5% $CO_2$.

HeLa cells were cultured the same way as NAR cells except for using DMEM (Dulbecco's Modified Eagle's Medium, Biological industries 500 mL, Catalog: 01-055-1A) instead of RPMI.

MCF10A cells were cultured at 37° C. and 5% $CO_2$ with medium containing ingredients same as with Hela cells and also: 1 mg/mL hydrocortisone suitable for cell culture (Sigma, Catalog number: H0888-1G), 10 mg/mL insulin from bovine pancreas powder (Sigma, catalog number: 16634-100 MG) with 1% acetic acid (FRUTAROM, Catalog: 5550030, and CAS no: 64-19-7), 1 mg/mL Cholera toxin *Vibrio cholera* (Sigma, Catalog number: C8052-.5MG), µg/mL 100 of EGF (Epidermal growth factor, Petro- Tech, E-Coli source, Catalog number: AF-100-15), 250 mL of F12 instead of FBS (Rhenium, Catalog number: 21765029) and 25 mL of US Donor Equine Serum (TAROM, catalog number: SH30074.03).

All of the results presented herein below represent an average and standard error of least three measurements.

Figure 1:
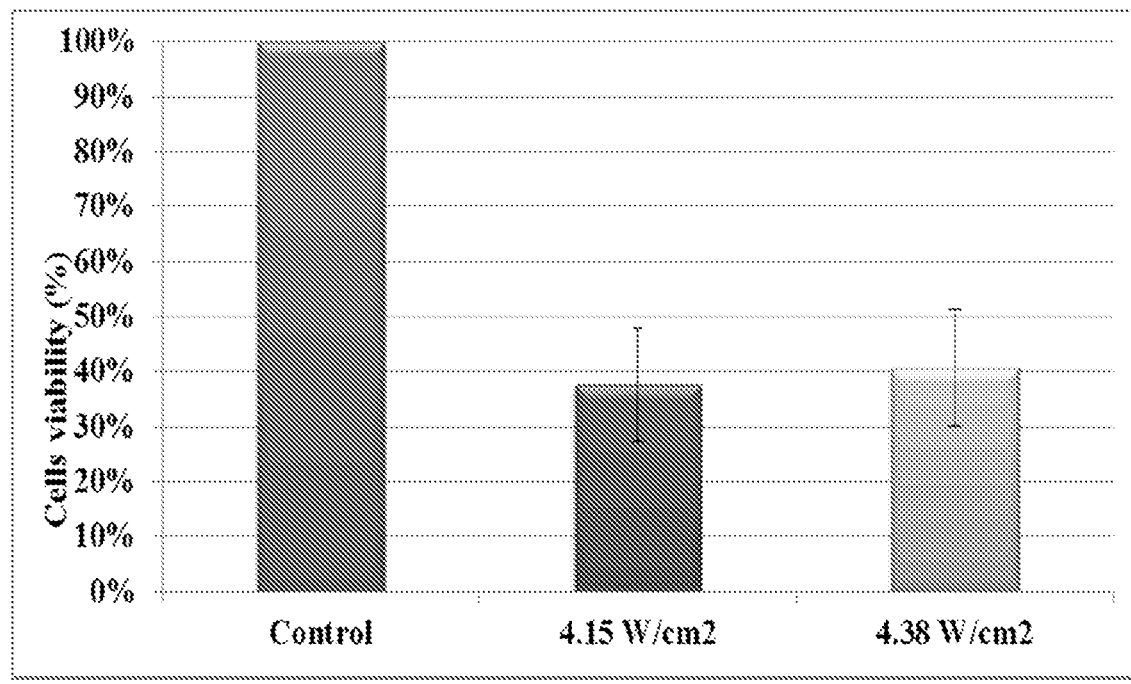
FIG. 1 shows HeLa cell type average viability after exposure to ultrasound (20 KHz and 50% duty cycle) for 1 minute at different intensities (1% and 3% amplitudes or 4.15 W/cm$^2$ and 4.38 W/cm$^2$, respectively). P value<0.1 compared to control experiment.

Initially, ultrasound intensities that would affect HeLa cells mortality were identified. Initial cells concentration before experiment was 160,000 cells/mL in all samples (determined by absorbance measurements, M-200 by TECAN, blank wavelength 670 nm reading subtracted from reading at 570 nm wavelength as described by Sigma procedure for MTT). FIG. 1 shows HeLa cell type average viability after exposure to ultrasound (20 KHz and 50% duty cycle) for 1 minute at different intensities (1% and 3% amplitudes). P value<0.1 compared to control experiment. In a control experiment cells were not exposed to ultrasound at any stage. FIG. 1 demonstrates that application of ultrasound (US) at the described parameters was below the cavitational threshold intensity, and caused about 60% mortality in Hela cells.

The effect of low intensity ultrasound on mortality of cancerous cells was further evaluated in NAR cell type. In this experiment low intensity ultrasound effects on NAR cell type was compared to MCF10A cell type that is considered as "healthy" (non-cancerous) cell type. The effects of ultrasound duration and intensity on MCF10A cells and NAR cells viability are presented in FIGS. 2 and 3 (presented as average standard deviation of at least three experiments). US frequency and duty cycle (DC) were set on 20 kHz and 50% respectively.

Figure 2:
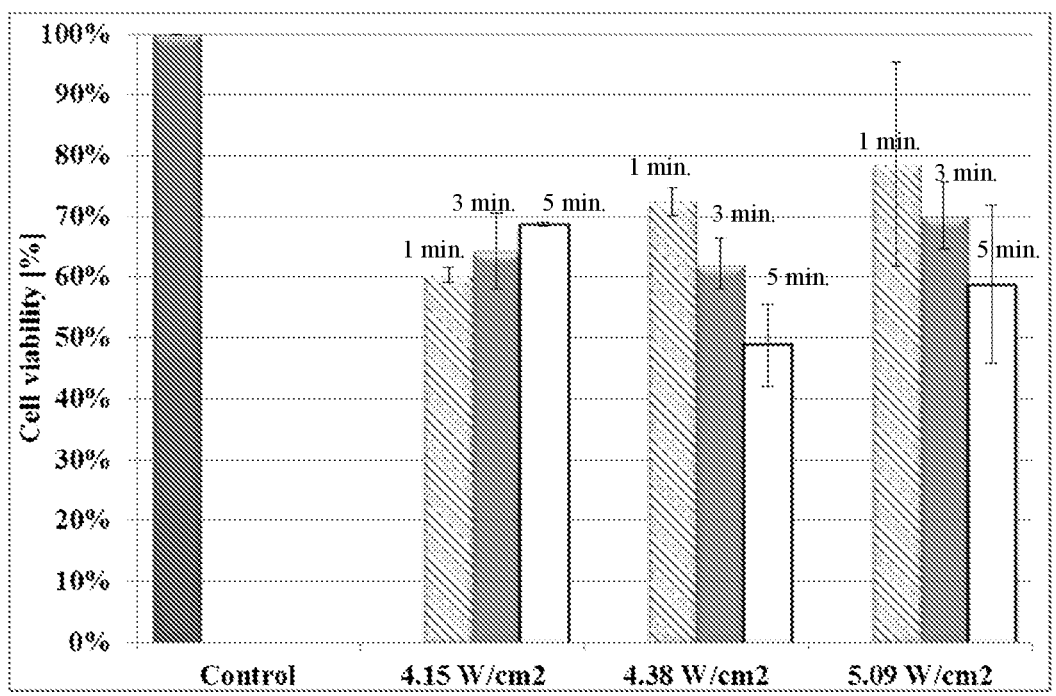
FIG. 2 shows MCF10A cell type average viability after exposure to ultrasound (20 KHz and 50% duty cycle) for different US intensities (1%, 3% and 5% amplitudes, or 4.15 W/cm$^2$, 4.38 W/cm$^2$ and 5.09 W/cm$^2$, respectively) and durations. P value<0.1 compared to control experiment.

FIG. 2 shows MCF10A cell type average viability after exposure to ultrasound (20 kHz and 50% duty cycle) for different ultrasound intensities and durations. P value<0.1 compared to control experiment.

Figure 3:
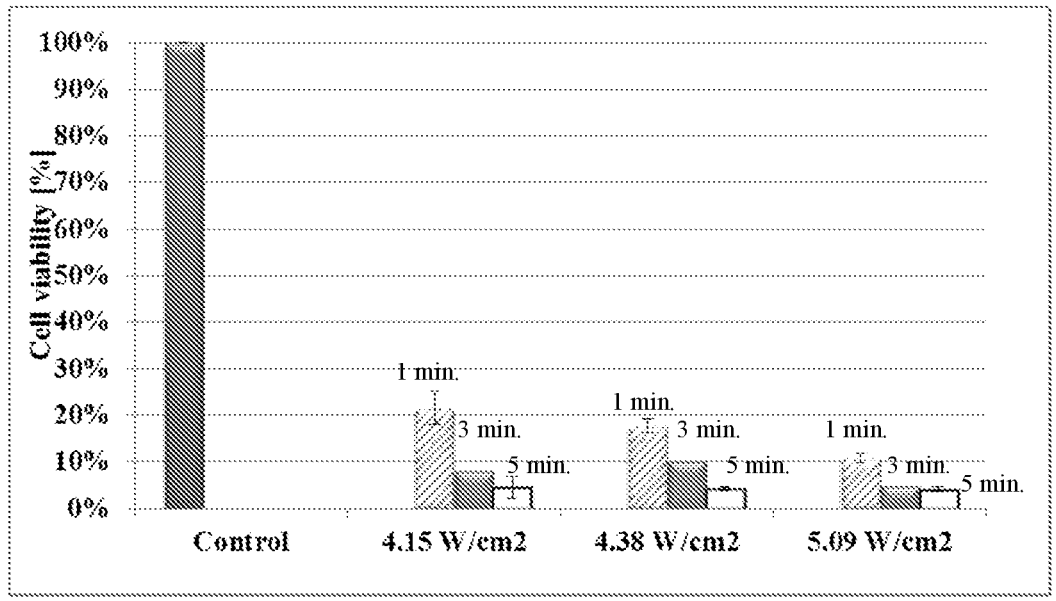
FIG. 3 shows NAR cell type average viability after exposure to ultrasound (20 kHz and 50% duty cycle) for different US intensities (1%, 3%, and 5% amplitudes or 4.15

FIG. 3 shows NAR cell type average viability after exposure to ultrasound (20 KHz and 50% duty cycle) for different ultrasound intensities. P value<0.1 compared to control experiment.

The effect of ultrasound duration and intensity on MCF10A and NAR cell types viability can be observed in FIGS. 2 and 3. The control column represents cells, which were not exposed to ultrasound any stage. Initial cells concentration was set to 160,000 cells/mL (determined by absorbance measurements, M-200 by TECAN, blank wavelength 670 nm reading subtracted from reading at 570 nm wave length as described by Sigma procedure for MTT). MCF10A cells were exposed to three different durations (1, 3 and 5 minutes) of ultrasound at two different intensities, while NAR cells were exposed to two different durations (1 and 5 minutes) of ultrasound at three different intensities. Fixed ultrasound parameters in all experiments were frequency of 20 kHz and 50% DC. These results demonstrate that application of ultrasound at the described parameters was below the cavitational threshold intensity.

The most dominant feature that can be observed from these figures is the fact that at any given ultrasound amplitude and duration, the mortality was higher for NAR cell type than MCF10A cell type, meaning that cancerous cells are much more sensitive to ultrasound exposure at low intensity. The average mortality of non-cancerous cells (MCF10A) was approximately 30% while the mortality of cancerous cells (NAR) was almost tripled and reaches approximately 80%.

The results also show that for MCF10A cells, mortality increased with the increase in duration of ultrasound exposure. Intensity wise, no trend was visible and also no statistical variance was found. This may be explained by the fact that the intensity was below the cavitational threshold intensity and that the increase in intensity was small (4.38 W/cm$^2$ and 5.09 W/cm$^2$ respectively). As for NAR cell type, at all amplitudes tested longer duration of ultrasound treatment resulted in higher NAR mortality. When ultrasound intensity was analyzed, a decrease in cell viability was observed with increase in US intensity, and as noted above all the intensities were below the cavitational threshold intensity.

To summarize, at all ultrasound intensities and exposure times tested, cancerous cells exhibited the highest mortality. NAR cells exhibited 80-95% mortality, Hela cells exhibited 60-65% mortality (at 1-minute exposure only), while the mortality observed in non-cancerous cells (MCF10A) was 20-30%.

Example 2: Effect of Ultrasound Duty Cycle (DC) on Viability of Cancerous Cell and of Normal Cells This study was conducted utilizing the most extreme ultrasound conditions of 5 minutes exposure at 5% amplitude (equals 5.09 W/cm$^2$). This intensity was below the cavitational threshold intensity. Ultrasound frequency in this study was set to 20 kHz. In all previous experiments, duty cycle (DC) was set at 50% to avoid thermal effect. In this study 10% and 90% DC were also evaluated for their effect on NAR and MCF10A cell types. Cell cultures were prepared as described in Example 1.

The effect of DC on cells viability can be observed in FIGS. 4 and 5.

FIG. 4 shows MCF10A cell type average viability after 5 minutes exposure to ultrasound (20 kHz) at 5% amplitude for different US duty cycles (10%, 50% and 90%). (P value<0.1 compared to control experiment.)

FIG. 5 shows NAR cell type average viability after 5 minutes exposure to ultrasound (20 kHz) at 5% amplitude for different US duty cycles (10%, 50% and 90%). (P value<0.1 compared to control experiment.)

FIGS. 4 and 5 indicate that both non-cancerous and cancerous cells were affected by ultrasound duty cycle. For both cell types, mortality increased with increased DC. In non-cancerous cells (MCF10A) mortality increased from 32% to 45% for 10% and 90% DC respectively, while in cancerous cells (NAR) the difference was much smaller, mortality increased from 94% to 96% for 10% and 90% DC respectively. This may suggest that mortality of cancerous cells at the ultrasound parameters that were used in this study, was already reaching the highest possible level, thus minimizing the effect.

The results of this study suggest that ultrasound DC can be used to control/minimize possible damage to healthy cells.

Example 3: In-Vivo Study in BALB C/J Mice Bearing KHJJ Mouse Breast Adenocarcinoma This study was carried out in BALB C/J white albino mice bearing KHJJ mouse breast adenocarcinoma. BALB C/J mice are infected by implantation under the skin of one of the mouse's thighs. A total of 18 mice were used, divided into three groups (6 mice per group, mixed genders). The three groups consisted of control group (group 1) and two groups assessing the effect of two different low intensity ultrasound protocols (groups 2 and 3). The second thigh (uninfected with cancer) in groups 2 and 3 serves as the reference organ. Group 1 was not being exposed to ultrasound at any stage. Group 2 and 3 were exposed to two different low intensity ultrasound protocols. Mice were anesthetized prior to ultrasound exposure with a formula containing Ketamine and Xylazine, administered in an amount depending on animal weight (Ketamine 75 mg/kg and Xylazine 5 mg/kg animal body weight).

The low intensity ultrasound protocols were determined by a preliminary experiments assessing which parameters (namely time, intensity and DC) do not induce injury to skin and internal organs (cavitational threshold intensity).

All mice in all groups were not being treated for about two weeks in order for the tumors to reach a desired initial volume (approximately 100 mm$^3$). After these two weeks, mice in groups 2 and 3 were exposed twice a week to predetermined low intensity ultrasound protocol on both thighs (with and without tumor). Each group was exposed to one protocol. The coupling medium for ultrasound exposures was an ultrasound gel (by MEDI-PHARM, England). The control group (group 1) was exposed to ultrasound gel for the same duration as groups 2 and 3 (without exposure to ultrasound). Body weights were measured three times a week and observational notes were taken for any changes in behavior or appearance.

Tumor volumes were measured using a caliper (to measure diameter of the tumor) three times a week (one day post ultrasound treatment) in order to assess the effect of ultrasound exposures on tumor's volume.

A proof-of-concept testing was done in laboratory mice with KHJJ tumor. The effect of US (20 kHz) exposure for 30 sec, 50% DC with two intensities (7.7 and 8.5 W/cm$^2$) on mice's tumor growth rate was assessed. US duration was reduced (compared to in vitro experiments) due to preliminary results showing mild damage to the skin, and the necessity to lower the intensity below the cavitational threshold intensity.

US was used in tandem with ultrasonic gel. In a control group, the mice were not insonated.

Blood was aspirated from mouse's tumor post mortem, allowing the fluid to clot at 37° C. for 2 hours, and was kept in a refrigerator for a further 2 hours to allow the clot to shrink, and was finally centrifuged at 7000 rpm for 5 minutes.

Exponential fit was assigned to each curve in FIG. 6. None of the treatments caused any visible damage to the insonated skin of both mice's flanks. The results shown in FIG. 6 show that the higher the US intensity used—the greater was the decrease in tumors growth rate (exponent value of 0.411>0.373>0.275 for control, 7.7 and 8.5 W/cm2 respectively). In addition, the tumor's stiffness was very different for insonated tumors compared to uninsonated. While the uninsonated tumors were quite rigid and whole, the insonated tumors were disintegrated and flaccid. Since large tumors develop necrotic cores and tumors were extracted when they reached a size of 1200 mm$^3$ or above, it was impossible to detect differences in histopathological samples of the tumors. However, the fluid that accumulated in the insonated tumors was tested and compared with blood of normal mice, and was found to differ greatly. This difference was further illustrated since the aspirated fluid from the tumor was not blood and it is assumed to be the content of cancerous exploded cells induced by the ultrasound exposure.

In summary, the in vivo experiment revealed two main features of insonating cancer tumors. The first feature is the reduced growth rate of the tumor as seen in FIG. 6 induced by insonation. The second feature is the disintegration of the cancer tumors as a result of cancerous cells explosion post insonation.

Example 4: Young's Modulus Measurements of Different Superficial Cancer Cell Types Young's modulus, also known as the elastic modulus of elasticity, offers a way to quantify mechanical differences between cells by measuring their deformability (as schematically shown in FIG. 7A and as exemplified in FIG. 7C). The higher Young's modulus, the stiffer the cell. The biomechanical properties of cells were evaluated by atomic force microscopy (AFM) for four different cell lines: non-cancerous cells (HaCaT), squamous cell carcinoma of the head and neck (HNSCC cells, UM-SCC47 and Cal33), and melanoma cells (A375).

Cell lines and culture condition were as follows. Human keratinocyte cell line, HaCaT, was grown in Minimal Essential Medium (MEM) and supplemented with 4.5 mM glucose, 10% (Vol) FBS, 1% (Vol) L-glutamine (2 mM), and 1% (Vol) penicillin-streptomycin (100 μg/mL penicillin and 100 μg/mL streptomycin) in a 5% $CO_2$ incubator, at 37° C. The cells were split every 2-3 days in order to prevent over-population as follows: the culture medium was removed from the flask and the cells were washed with filtered Phosphate-buffered saline (PBS). Cells were disconnected from the flask after the addition of 2 mL trypsin-EDTA and incubation of 10 minutes in the incubator. Following incubation, 10 mL growth medium (MEM) was added. The suspended cells were pipetted 3-6 times and divided into 3 flasks (4 mL each). Fresh medium was added to a total volume of 12 mL in each flask. The cells were returned to the incubator for 3 days for further proliferation. The MEM growth medium was replaced by Dulbecco's Modified Eagle Medium (DMEM) medium for the cell lines Cal33 (human, tongue SCC), Cal33-GFP (human, tongue SCC, expressing green fluorescent protein (GFP)), UM-SCC47 (human, tongue SCC), and UTC-SCC60A (human, tonsillar SCC). For the cell lines KYSE-180 (human, esophageal SCC), SNU-1076 (human, laryngeal SCC), and A375 (human, malignant melanoma) the MEM growth medium was replaced by RPMI medium.

The cells were subjected to atomic force microscopy (AFM) measurements, as follows. Measurements were carried out with a JPK Nanowizard ultra-speed atomic force microscope (Bruker, Berlin, Germany) mounted on an inverted optical microscope (Axio Observer; Carl Zeiss, Heidelberg, Germany). Borosilicate spherical AFM probes (diameter=~2 μm; NovaScan, USA) attached to silicon triangular cantilevers with a nominal spring constant of 0.1 N/m were used. Spring constant of the cantilever was determined experimentally by measuring the thermal fluctuations, as described e.g. in Hutter, Jeffrey L., and John Bechhoefer. "Calibration of atomic-force microscope tips." Review of scientific instruments 64, no. 7 (1993): 1868-1873. Cells were seeded on 35 mm TPP tissue culture dishes (80,000 cells/mL) and incubated for 24 hours. After 24 hours, the growth media was replaced, and the cells were analyzed. To properly maintain the cells, a temperature of 37° C. was maintained during the entire duration of the measurements using a microincubator perfusion chamber (PetryDishHeater, JPK instruments, Bruker, Germany), which holds a 35 mm cell culture dish attached to the microscope stage. Using an optical bright-field microscope, isolated cells were selected for analysis to avoid possible influence of neighboring cells on the cell mechanical properties. The stiffness of the cells was determined based on indentation-type experiments, as previously described, e.g. in Lekka, Małgorzata. "Discrimination between normal and cancerous cells using AFM." Bionanoscience 6, no. 1 (2016): 65-80. Briefly, for each indentation measurement, a total of 60 force-distance curves from three (3) perinuclear locations on the cell surface at a loading rate of 0.5-1 µm/sec were obtained. The maximal applied loading force in each measurement was ~0.2-0.6 nN. Young's modulus was calculated by fitting a modified Hertz model, e.g. as described by Vinckier, Anja, and Giorgio Semenza. "Measuring elasticity of biological materials by atomic force microscopy." FEBS letters 430, no. 1-2 (1998): 12-16, to the force-distance curves. With this method, it is possible that repeated applications of force might irreversibly damage the sample, or, alternatively, that the loading rate might affect the measured stiffness. Therefore, for each measurement consisting of ~60 force-distance curves, the measured point stiffness derived from each curve was plotted as a function of the measurement number and as a histogram. During each experiment, the measured stiffness values derived from the individual force-distance curves were found to distribute normally around a mean, which suggests that the cell did not undergo irreversible deformation during measurement. Data analysis was carried out using MATLAB software (The Math Works, Natick, MA).

As can be seen in FIG. 7D, the average Young's modulus of HaCaT (healthy) cells is ~35 KPa, which is significantly higher than the average Young's modulus of UM-SCC47 (~25 KPa), Cal33 (~5 KPa), and A375 (~1.6 KPa).

Actin network, formed by actin filaments (F-actin) or stress fibers, usually significantly contributes to the mechanical stability (elasticity/stiffness) of living cells, and modifications of the actin cytoskeleton during the metastatic process may correlate with the cell malignancy. The arrangement of fluorescently labeled F-actin filaments in HaCaT, Cal33, and A375 cells was visualized by confocal fluorescence images of F-actin in order to examine whether the differences in their network structure can be attributed to the observed difference in their mechanical behavior.

For confocal fluorescence imaging of F-actin, cells were grown and seeded (10,000 cells per 200 µL medium) in µ-slide 8 well glass bottom plate. The medium was removed 24 hours later, and the cells were fixed immediately with 200 µL of diluted 4% Paraformaldehyde (PFA) in PBS. After 10 minutes of incubation at room temperature, the PFA was washed three times with 300 µL PBS. The cells were permeabilized for 2 minutes with 200 µL of 0.1% triton×100 with 1:50 phalloidin in PBS. The filamentous actin (F-actin) was labeled with phalloidin-iFluor 555 reagent. After 10 minutes of incubation at room temperature (R.T.), the well was washed twice with 300 µL PBS each time and afterwards, for nuclei staining, mounting medium with 4',6-diamidino-2-phenylindole (DAPI) was added. Fluorescence images were obtained using a confocal microscope (Zeiss LSM880 Airyscan).

Figure 7F:
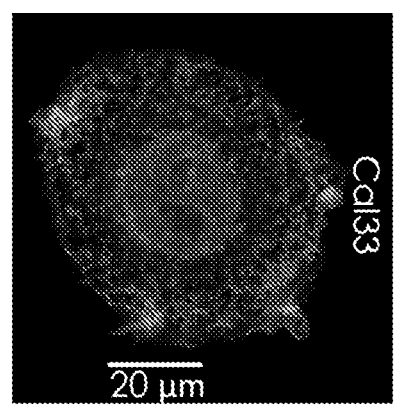
Figure 7G:
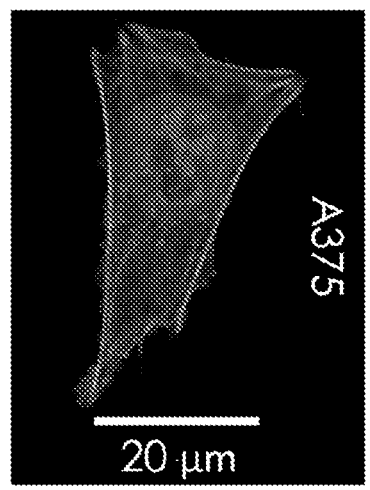

As can be seen in FIGS. 7E, 7F and 7G, HaCaT cells possess a pronounced network of actin filaments, which are localized in the peripheral region of the cell. On the other hand, in Cal33 and A-375 cells there are fewer actin filaments, and the actin structures form a more disorganized and cross-linked network with no patterns, which could be a contributing factor for their low Young's modulus.

Example 5: Correlation Between Cells Sensitivity to US and their Young's Modulus After establishing the modulus of elasticity for the different cell types, the question whether it can predict their sensitivity to ultrasound (US) was addressed. In an attempt to answer this question, the HNSCC cell line Cal33 and the healthy human keratinocyte cell line HaCaT were exposed to different US operating conditions, to find US parameters that cause damage mainly to the cancerous cells. FIG. 8A is a schematic presentation of the experimental setup, which also enabled cell viability measurements following US exposure.

The in vitro cell viability assay was performed as follows. Cells were seeded at the desired density in a 12-well plate (each well contained 1 mL of culture medium). The culture medium was removed after 24 hours of incubation and cells were washed with filtered PBS. Wells were filled with 100 µL Presto Blue (PB) cell viability reagent and 900 mL MEM medium and incubated in the incubator for 10 min. Then, samples (200 µL of PB and medium from each one of the wells of the 12-well plate) were transferred to wells in a black 96-well plate (three repetitions). Cell viability was measured by measuring the fluorescence in each one of the wells, using a microplate reader spectrophotometer (Infinite M200, TECAN) at an excitation wavelength of 560 nm and emission at 590 nm. The blank solution contained growth medium and PB (at volume ratio 9:1).

Measuring the ultrasound effect on cells viability in vitro was carried out as follows. Cells were seeded at the density of 160,000 cells/mL in a 12-well plate (each well contained 1 mL of culture medium) and the cell viability was tested using the PB reagent as described above. Afterwards, the plate was washed with filtered PBS, filled with 1 mL of fresh medium and placed in a 16 cm diameter plate horn (QSONICA, 700 W, 20 KHz) transducer container filled with 4 cm (height) of degassed water as schematically shown in FIG. 8A. All plates were identically placed to precisely assure the same position for efficient repetitions of the experiments. The US conditions for all experiments were at intensities of 0.139-0.164 W/cm$^2$, for 20 and 40 sec with 50% duty cycle. After US exposure, the plates were incubated for 1 hour at 37° C. and 5% $CO_2$ and then the same PB cell viability procedure was performed. Viability percentage after US exposure (treated cells) was calculated as a percentage out of the same well's cell viability before US exposure (untreated cells is referred to as 100% viability).

Four US energy levels were tested in this experiment: 2.8, 3.3, 5.6 and 6.6 J/cm$^2$, corresponding to US parameters of 20 KHz, 0.139 and 0.164 W/cm$^2$, 20 and 40 sec exposure time, respectively, and operation mode of 50% duty cycle.

As can be seen in FIG. 8B, there was a significant difference between the viability of healthy cells (HaCat) and of cancer cells (Cal33), at all the US energy levels evaluated (interaction<0.0001; row factor<0.0001; column factor<0.0001). In particular, US energy level of 0.139 J/cm$^2$ (2.8 J/cm$^2$ as indicated in FIG. 8B) did not affect HaCaT cells' viability (~95%) while at these same conditions, Cal33 cells' viability decreased dramatically (~27%). Since higher US energy levels affected HaCaT cell line (around 50% of cell viability), the effect of 0.139 J/cm$^2$ US energy level was examined on the viability of additional superficial cancer cell lines.

FIG. 8C demonstrate the viability percentage of two human HNSCC cell lines (namely Cal33 and UM-SCC47), human epithelial melanoma cell line (A375), and the (healthy) human keratinocyte (HaCaT) cell lines. At the above-detailed operating conditions (namely at the US energy level of 0.139 J/cm$^2$), the observation shown in FIG. 8B was reinforced in a broader set of tumor cells, showing the non-cancerous HaCaT cells were less sensitive to and less affected by US (viability of ~95%) compared to the HNSCC lines (~30% to 50%) and malignant melanoma cells (~20%). It is important to note that in addition to the US ability to distinguish between healthy and cancer cells, these results also demonstrated that various cancer cell types exhibited different sensitivity to the same US application. Notwithstanding the above, the increased sensitivity to US energy as compared to healthy cells was common to all of the tested cancer cells. Finding a non-molecular cellular parameter, such as a biomechanical property (i.e. modulus of elasticity) that can distinguish between cancer and healthy cells, can promote an altered path of personalized targeted cancer therapy. FIG. 8D is a graph that represents the cell viability percentage as a function of the cell's Young's modulus at a specific US energy level (namely 0.139 $J/cm^2$) for four different cell lines. As can be seen in FIG. 8D, the observed differences in cell viability following US application correlate with their elasticity. In other words, a cell line characterized by a low Young's modulus value is also characterized by a relatively low viability. Without wishing to be bound by theory, these results support show that a single biomechanical property can predict the sensitivity of the cell to US treatment.

Example 6: US Treatment Delays Tumor Progression In Vivo

In order to validate US potential as a treatment means for superficial cancer in tumor-bearing mice, a safety study was initially conducted, evaluating the effect of the US on normal skin. An ultrasound (US) application protocol that was previously tested (as described in Zimon, Rinat Lifshiz, Galya Lerman, Einat Elharrar, Tal Meningher, Aviv Barzilai, Ramesh Moamen Masalha, Chintakunta et al. "Ultrasound targeting of Q-starch/miR-197 complexes for topical treatment of psoriasis." *Journal of Controlled Release* 284 (2018): 103-111) was used and was found safe for SCID mice, at 3 min operation time, intensity of 12.3 $W/cm^2$, and 50% duty cycle (energy level of about 340 $J/cm^2$).

Briefly, for the safety experiments, healthy NOD/SCID mice aged 6-week-old (n=2) were treated with US at 12.3 $W/cm^2$ intensity for 3 min at 50% duty cycle. Immediately after treatment, samples of the exposed skin were taken to histology examination. In addition, for the evaluation of US effect on tumor reduction, different US intensities (10.5, 11.5, and 12.3 $W/cm^2$) and repetitions (twice a day (TD), every day (ED) and every other day (EOD)) during 1 min at 50% duty cycle, were applied. A total of 43 mice were divided randomly into the following groups: (I) no treatment (control) (n=9); (II) 10.5 $W/cm^2$, EOD (n=4); (III) 11.5 $W/cm^2$, EOD (n=4); (IV) 12.3 $W/cm^2$, EOD (n=10); (V) 12.3 $W/cm^2$, ED (n=7); (VI) 12.3 $W/cm^2$, TD (n=9). During the experiments, the tumor width and length (diameters) were measured manually using a caliper. Tumor volume was calculated using the ellipsoid volume equation under the assumption that the depth of the tumor is equal to the smaller diameter value. After two days, 3 mice from groups I, IV, and V, and 4 mice from group VI, were sacrificed. After 11 days, 3 mice from groups I and IV, 4 mice from group V, and 5 mice from group VI were sacrificed. After 15 days of treatment, 3 mice from group I, and 4 mice from groups II, III, and IV were sacrificed. The tumors were removed and washed with PBS. All the tumors were weighed (except for the tumors that were taken after two days for necrosis analysis) and transferred into 4% (w/v) paraformaldehyde (PFA) in PBS for 1 h/1 $mm^3$ of tumor volume. Afterwards, all the tumors were transferred into 70% ethanol until histology was executed.

Since the aim was to evaluate US effect in vivo, in which the US energy needs to be transferred through a dense tissue rather than through aqueous medium, the energy level applied for the in vivo experiments was two orders of magnitude higher than the energy level used in the in vitro experiments (namely the experiments performed with cells). As can be seen in FIG. 9A and in FIG. 9B, for these conditions, no external skin damage and no evidence of pathological abnormalities were observed.

Examination of US treatment effect on tumor reduction in vivo was carried out as described above and as previously described by Azagury R. et al. *Ultrasound Med Biol.* 2016; 42 (7): 1560-1567. doi: 10.1016/j.ultrasmedbio.2016.02.005, the study IL-80-12-2015 was approved by the IRB for animal welfare. Briefly, NOD/SCID mice aged 6-week-old were injected subcutaneously (S.C.) with 1×106 HNSCC cell line (Cal33) per 100 μL of PBS at two points on the mice's back. The US treatments were initiated when the tumors reached 3-5 mm in diameter (about one week after the injection), measured manually by a caliper. Tumors that did not reach the appropriate size, were not taken into account. For the US treatment, a glass cylinder chamber (at 1.6 cm diameter) was placed on the mice back above the tumor and filled with 3 mL of ultrasonic gel (at a temperature of ~4° C.). The US probe was positioned 1 cm from the surface of the skin without touching the chamber walls. The US (QSONICA, 700 W, 20 KHZ) conditions were at intensity range of 10.5-12.3 $W/cm^2$, for 1-3 min with 50% duty cycle, and probe diameter of 1.3 cm. Mice were anesthetized by injection of ketamine at 100 mg/Kg and xylazine 10 mg/Kg before application of US. Groups that were exposed to US more than once at the same day, were connected to the isoflurane anesthetic system (SomnoSuite, low-flow anesthesia system, from Kent Scientific Corporation) through the second sonication procedure. In order to minimize US thermal effect, the ultrasonic gel was replaced with fresh gel every 30 sec. During the procedure, before US application, the gel was kept inside an ice water bowl. After US was turned off, the skin was cleaned with Septol.

In other words, for the efficacy study, tumorigenic Cal33 cell line was injected under the skin of NOD/SCID mice. When the tumor reached 3-5 mm in diameter, three different US intensities were applied, 10.5, 11.5, and 12.3 $W/cm^2$, for 1 min at 50% duty cycle every other day, and tumors' volume and mass were measured and calculated respectively (see FIG. 9C for experimental protocol).

As shown in FIG. 9D, all three groups of mice that were exposed to US experienced delayed tumor growth when compared to the untreated group, in particular from the 11th up to the 15th day of the experiment. Specifically, on the 15th day, the average tumor volume of the experimental group that was exposed to 12.3 $W/cm^2$ was significantly, P=0.0092 (~two times) lower than that of the control group.

In addition to the tumor volume measurement, at the end of the experiment the tumor mass of the four experimental groups was measured (FIG. 9E). As can be seen, there was a significant statistical difference between the untreated group and all of the three groups that were exposed to US treatment, where the lowest average tumor mass was demonstrated in the group treated with 12.3 $W/cm^2$ (IV). It is important to mention that none of the US treatments caused any visual damage to the exposed skin. Moreover, it should be emphasized that complete disappearance of one of the tumors from the group treated with 12.3 $W/cm^2$ was observed. Furthermore, evaluating the representative florescence images of Cal33-GFP tumor sections expressing green fluorescent protein, as shown in FIGS. 9F and 9G, reduced GFP fluorescent signal was observed in US treated tumors (FIG. 9G) compared to control (FIG. 9F).

An additional step for progressing to in vivo experiments, is optimizing the US protocol to achieve the highest efficiency (i.e. tumor reduction at shortest time), by altering the number of repetitive treatments for each tumor. Therefore, the most promising and safe US conditions found for the efficacy experiment (i.e. 12.3 W/cm$^2$, 1 min of exposure time and 50% duty cycle) were next explored as a repetitive treatment protocol (ones every other day, once a day, and twice a day), on tumor progression in mice bearing a Cal33 tumor.

Tumor volume growth kinetics shown in FIG. 10A indicate that the repetition of US treatment is associated with an enhanced reduction in tumor's volume (and consequently growth). As shown in FIG. 10B, the major difference in tumor volume and mass was obtained between the control group and the group exposed to US twice a day (group VII).

Example 7: US Treatment Induced Necrosis in Tumors

In order to gain further understanding of the effect of US on tumor mass and volume reduction, cross-sections of all of the tumor subjected to the above-detailed treatment were evaluated by a pathologist.

The visual difference of AON (area of necrosis) between the control and treated groups (twice a day, 48h and 11 days from first exposure) is presented in FIG. 11. As clearly shown in FIG. 11, the AON of the control is smaller than the AON of the treated groups, furthermore the AON increases with the days of treatment. Moreover, there is a presence of lymphocytes and fibroblasts cells in both control and treated groups while atypical mitosis (malignant tumor cell) is present only in the control.

Values and Mean AONs of the different groups, after 48 h and 11 days, are presented in FIG. 12A and FIG. 12B, respectively. After 11 days, the difference between the twice a day group and the control group was statistically significant (p=0.0228), likewise the difference between the twice a day group and every other day group (p=0.0176). In particular, as can be seen in FIG. 12C, for twice a day US treatment, the area of necrotic tissue (AON) increased as a function of time (48 h to 11 days). The largest value of mean AON was observed for the twice a day group and the smallest value of AON obtained for the control group. For more frequent repetitive treatment, the percentage of AON obtained was higher. The difference between the twice a day group and the control group was statistically significant (20 times higher than control for the twice a day after 11 days), likewise the difference between the twice a day group and every other day group. All the histology results were consistent with the in vivo experiments: the best tested US operation conditions, after 11 days of treatment, which present the highest AON % and lowest tumor volume and mass were twice a day at the highest US intensity (12.3 W/cm$^2$).

Histology was performed as follows. For Histopathological preparation 4% (w/v) formalin-fixed paraffin-embedded HNSCC tumors were cut to 4 μm sections, mounted on microscope glass slides and heated overnight at 65° C. in a drying oven. Following dehydration, slides were stained with hematoxylin and eosin (H&E), scanned by Panoramic MIDI II scanner (3D Histech), and analyzed by a pathologist. Necrotic areas within treated tumors were morphologically evaluated. First, the necrotic area was marked and the area of necrosis (AON) calculated in arbitrary units (AU) using image j and case viewer programs, after which the percentage out of the entire tumor volume was calculated (AON %). Morphologic characteristics of necrosis consisted of areas of fibrin, acute inflammation and tissue loss. Results are presented in AON %. Statistical analysis was carried out by GraphPad Prism 7.03 software, significance set at p=0.05.

The invention claimed is:

1. A method of treating a subject suffering from a disease or a disorder associated with hyperproliferating cells, said method comprising non-invasively irradiating a tissue comprising said hyperproliferating cells in said subject with ultrasound, said ultrasound having a frequency between 20 and 200 kHz, at an intensity between 0.5 and 100 W/cm$^2$, provided that the intensity is characterized by a low-frequency mechanical index of between 1 and 2.5, wherein said intensity produces a mechanical index lower than 2.5, and wherein said method comprises evaluating a mechanical stiffness of said hyperproliferating cells, prior to said irradiating, and adjusting said intensity based on said evaluating.

2. The method according to claim 1, wherein said evaluating comprises obtaining a ratio between elasticity values of said hyperproliferating cells and healthy tissue cells obtained from a vicinity of said hyperproliferating cells.

3. The method according to claim 2, wherein said elasticity values are obtained by determining Young's modulus of said hyperproliferating cells in a sample obtained from said subject.

4. The method according to claim 2, wherein said elasticity value of said healthy tissue cells is determined based on reference values of Young's modulus characteristic of said healthy tissue cells.

5. The method according to claim 1, wherein said evaluating is performed by atomic force microscopy.

6. The method according to claim 1, wherein said evaluating is performed by confocal microscopy with F-actin staining.

7. The method according to claim 1, wherein said adjusting of the intensity comprises determining a maximal intensity producing a mechanical index of 2.5, and administering the ultrasound at an intensity of between 1 and 40% of the maximum intensity if a ratio of elasticity values is between 0.01 and 0.15, administering ultrasound at an intensity of between 10 and 80% of the maximum intensity if the ratio of elasticity values is between 0.15 and 0.35, and administering ultrasound at an intensity of between 25 and 100% of the maximum intensity if the ratio of elasticity values is between 0.35 and 0.7.

* * * * *